(12) United States Patent
Kinsho et al.

(10) Patent No.: US 7,202,318 B2
(45) Date of Patent: Apr. 10, 2007

(54) POLYMERIZABLE FLUORINATED ESTER, MANUFACTURING METHOD, POLYMER, PHOTORESIST COMPOSITION AND PATTERNING PROCESS

(75) Inventors: Takeshi Kinsho, Joetsu (JP); Takeru Watanabe, Joetsu (JP); Seiichiro Tachibana, Joetsu (JP); Jun Hatakeyama, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/175,346

(22) Filed: Jul. 7, 2005

(65) Prior Publication Data
US 2006/0009602 A1   Jan. 12, 2006

(30) Foreign Application Priority Data
Jul. 9, 2004   (JP) .............................. 2004-203195

(51) Int. Cl.
*C08F 12/20*   (2006.01)
(52) U.S. Cl. ...................... 526/242; 526/245; 526/319; 560/205; 560/219
(58) Field of Classification Search ................ 526/245, 526/247, 319, 242; 560/205, 221, 219
See application file for complete search history.

(56) References Cited

U.S. PATENT DOCUMENTS

| 4,578,508 A * | 3/1986 | Griffith et al. .............. 560/221 |
| 6,784,312 B2 | 8/2004 | Miyazawa et al. |
| 6,800,414 B2 | 10/2004 | Nishimura et al. |
| 6,800,418 B2 | 10/2004 | Yoon et al. |
| 2003/0078352 A1 * | 4/2003 | Miyazawa et al. .......... 526/245 |
| 2003/0157430 A1 * | 8/2003 | Yoon et al. .............. 430/270.1 |
| 2003/0224283 A1 * | 12/2003 | Allen et al. .............. 430/270.1 |

FOREIGN PATENT DOCUMENTS

| JP | 2002-72484 A | 3/2002 |
| JP | 2003-40840 A | 2/2003 |
| JP | 2003-192729 A | 7/2003 |

OTHER PUBLICATIONS

Trinque et al. "Vacuum-UV influenced design of polymers and dissolution inhibitors for next generation photolithography", Journal of Fluorine Chemistry, vol. 122, (2003), pp. 17-26.*

T. Nakai et al., Tetrahedron Letters, vol. 29, No. 33, p. 4119-4122, 1988.
T. Nakai et al., Organic Syntheses, vol. 76, p. 151-158, 1998.
B.C. Trinque et al., *Journal of Flourine Chemistry*, vol. 122, (2003), pp. 17-26.

* cited by examiner

*Primary Examiner*—Ling-Sui Choi
*Assistant Examiner*—Michael Bernshteyn
(74) *Attorney, Agent, or Firm*—Birch, Stewart, Kolasch & Birch, LLP

(57) ABSTRACT

Polymerizable fluorinated ester compounds having formula (1) or (2) are novel wherein $R^1$ is H, methyl or trifluoromethyl, $R^2$ is a divalent hydrocarbon group, $R^3$ is H or a monovalent hydrocarbon group, or $R^2$ and $R^3$, taken together, may form a ring, $R^4$ is H, OH or a monovalent hydrocarbon group, and $R^5$ is an acid labile group. They are most useful as monomers to produce polymers for the manufacture of radiation-sensitive resist compositions

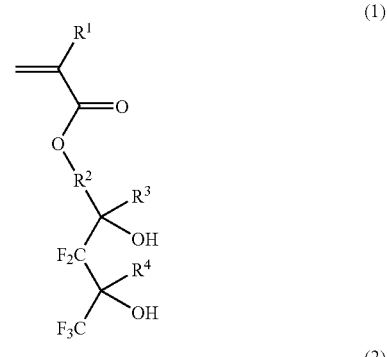

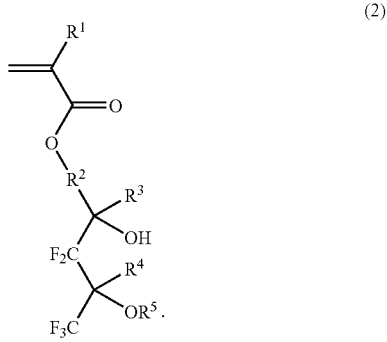

5 Claims, No Drawings

POLYMERIZABLE FLUORINATED ESTER, MANUFACTURING METHOD, POLYMER, PHOTORESIST COMPOSITION AND PATTERNING PROCESS

CROSS-REFERENCE TO RELATED APPLICATION

This non-provisional application claims priority under 35 U.S.C. §119(a) on Patent Application No. 2004-203195 filed in Japan on Jul. 9, 2004, the entire contents of which are hereby incorporated by reference.

1. Technical Field

This invention relates to novel polymerizable fluorinated ester compounds and processes for preparing the same. The polymerizable fluorinated ester compounds are useful as raw materials for the synthesis of functional materials, pharmaceutical and agricultural chemicals, and most useful as monomers to produce polymers for the manufacture of radiation-sensitive resist compositions which are fully transparent to radiation having a wavelength of up to 500 nm, especially up to 300 nm, typically KrF, ArF and $F_2$ laser beams, and have good resistance to dry etching.

The invention also relates to methods for preparing the ester compounds, polymers comprising recurring units derived from the ester compounds, photoresist compositions comprising the polymers, and a patterning process using the photoresist compositions.

2. Background Art

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF, ArF or $F_2$ laser as the light source is strongly desired to reach the practical level as the micropatterning technique capable of achieving a feature size of 0.3 µm or less. Various alkali-soluble resins are used as the base resin in such resists.

For KrF laser resists, a polyhydroxystyrene resin having phenolic hydroxyl groups as the alkali-soluble functional group is, in fact, a standard base resin. For ArF laser resists, poly(meth)acrylate resins using carboxyl groups as the alkali-soluble group and resins comprising polymerized units of cycloaliphatic olefin such as norbornene are under investigation. Of these, the poly(meth)acrylate resins are regarded, due to ease of polymerization, as a promising candidate that will find practical use. For these resist resins using as the alkali-soluble functional group carboxyl groups having a higher acidity than phenolic hydroxyl groups, however, an outstanding issue is difficulty of dissolution control, often leading to pattern collapse caused by swelling or the like.

Functional groups having an acidity comparable to phenolic hydroxyl groups are desired. It was proposed to use an alcohol having a plurality of fluorine atoms substituted at α- and α'-positions (e.g., having a partial structure: —$C(CF_3)_2$OH) as the alkali-soluble functional group, as described in G. Wallraff et al., Active Fluororesists for 157 nm lithography in 2nd International Symposium on 157 nm Lithography. Styrene and norbornene derivatives having fluoroalcohol —$C(CF_3)_2$OH incorporated therein are proposed as monomers used in the manufacture of base resins. Similar examples of fluoroalcohol-substituted norbornene are found in JP-A 2003-192729 and JP-A 2002-72484. For the polymerization of norbornene monomers, however, radical polymerization of monomers of the same type is difficult, and instead, special polymerization techniques such as coordinate polymerization and ring-opening metathesis polymerization using unique transition metal catalysts are necessary. Although alternating copolymerization between a norbornene monomer and a comonomer such as maleic anhydride or maleimide can be implemented by radical polymerization, the presence of comonomer imposes a substantial limit on the freedom of resin design.

JP-A 2003-040840 describes fluoroalcohol-substituted acrylate monomers. Although the method of preparing these monomers is not definite, the starting reactant used is hexafluoroacetone (boiling point −27° C.) which is awkward to handle because it is gaseous at room temperature. The synthesis of polymerizable compound must follow long steps, leaving the problem that commercial preparation is difficult.

There is a strong demand to develop a polymerizable compound which is industrially amenable and which has both a (meth)acrylate structure that facilitates the preparation or polymerization of a resist resin and a functional group that has an acidity comparable to phenolic hydroxyl.

DISCLOSURE OF THE INVENTION

An object of the present invention is to provide novel polymerizable fluorinated ester compounds which are useful monomers for the preparation of polymers to be formulated in resist compositions having high transparency to laser radiation with a wavelength of up to 500 nm, especially up to 300 nm, high dry etching resistance, and an excellent development behavior, and which compounds can be prepared from reactants that are readily available and easily manageable.

Other objects are to provide methods for preparing the ester compounds, polymers comprising recurring units derived from the ester compounds, photoresist compositions comprising the polymers, and a patterning process using the photoresist compositions.

The inventor has found that polymerizable fluorinated ester compounds having the general formulae (1) and (2), shown below, can be prepared from readily available reactants by the method, described later, in high yields and in a simple manner; that these ester compounds are polymerizable by industrially easily implementable polymerization techniques such as radical polymerization; and that using a polymer resulting from the polymerization as a base resin, a radiation-sensitive resist composition having high transparency to radiation with a wavelength of up to 300 nm, high etching resistance and excellent development behavior is obtainable.

Thus the present invention provides polymerizable fluorinated ester compounds, making methods, polymers, photoresist compositions, and a patterning process, as defined below.

In a first aspect, the present invention provides a polymerizable fluorinated ester compound having the general formula (1) or (2).

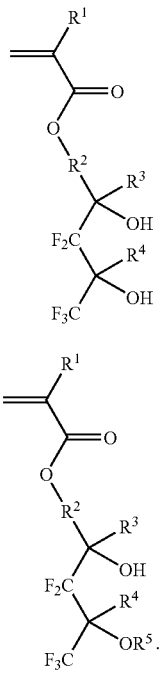

(1)

(2)

Herein $R^1$ is hydrogen, methyl or trifluoromethyl, $R^2$ is a straight, branched or cyclic, divalent hydrocarbon group of 1 to 15 carbon atoms, $R^3$ is hydrogen or a straight, branched or cyclic, monovalent hydrocarbon group of 1 to 15 carbon atoms, or $R^2$ and $R^3$, taken together, may form a ring with the carbon atom to which they are attached, $R^4$ is hydrogen, hydroxyl or a straight, branched or cyclic, monovalent hydrocarbon group of 1 to 15 carbon atoms, and $R^5$ is an acid labile group.

In preferred embodiments, $R^2$ is a divalent hydrocarbon group containing a cycloaliphatic hydrocarbon of 5 to 12 carbon atoms; $R^2$ is —$(CH_2)_n$— wherein n is an integer of 1 to 8; $R^2$ and $R^3$, taken together, form a trivalent cycloaliphatic hydrocarbon group of 5 to 12 carbon atoms with the carbon atom to which they are attached.

In a second aspect, the present invention provides a method for preparing a polymerizable fluorinated ester compound, comprising the steps of reacting a carbonyl compound having the general formula (3) with 1,1,3,3,3-pentafluoro-2-propenyl oxide to form a compound having the general formula (4), and reacting the compound having formula (4) with a compound $R^4$-Z to form a polymerizable fluorinated ester compound having the general formula (1).

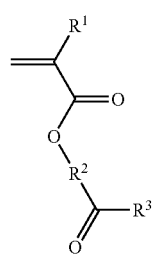

(3)

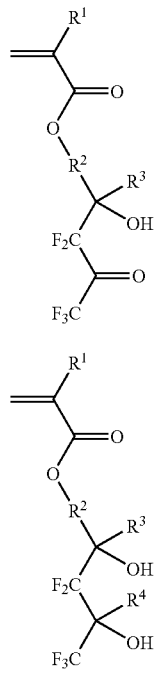

(4)

(1)

Herein $R^1$ to $R^4$ are as defined above, and Z is such a monovalent group that $R^4$-Z provides a $R^4$ anion equivalent.

The present invention also provides a method for preparing a polymerizable fluorinated ester compound, comprising the step of acylating an alcohol compound having the general formula (5) to form a polymerizable fluorinated ester compound having the general formula (1).

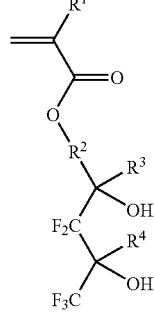

(5)

(1)

Herein $R^1$ to $R^4$ are as defined above.

In a third aspect, the present invention provides a polymer comprising recurring units having the general formula (1a) or (1b).

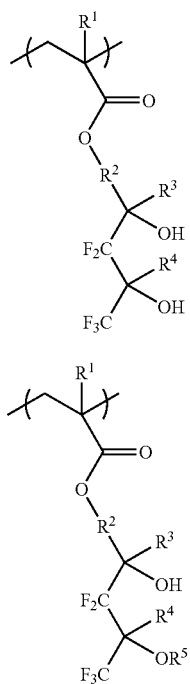

(1a)

(2a)

Herein $R^1$ to $R^5$ are as defined above.

In a preferred embodiment, the polymer may further comprise recurring units having the general formula (6a):

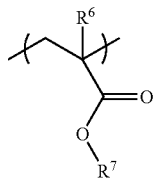

(6a)

wherein $R^6$ is hydrogen, methyl or trifluoromethyl, and $R^7$ is an acid labile group, the polymer having a weight average molecular weight of 2,000 to 100,000.

In a fourth aspect, the present invention provides a photoresist composition comprising (A) the polymer defined above, (B) a photoacid generator, and (C) an organic solvent.

In a fifth aspect, the present invention provides a process for forming a pattern, comprising the steps of applying the photoresist composition defined above onto a substrate to form a coating; heat treating the coating and exposing the coating to high-energy radiation with a wavelength of up to 300 nm or electron beam through a photomask; optionally heat treating the exposed coating, and developing the coating with a developer.

The present invention offers polymerizable fluorinated ester compounds which are novel. These polymerizable fluorinated ester compounds are useful reactants for functional materials, pharmaceutical and agricultural chemicals. In particular, they are very useful monomers for polymers which are formulated in radiation-sensitive resist compositions having high transparency to radiation with a wavelength of up to 500 nm, especially up to 300 nm, and an excellent development behavior owing to the inclusion of phenol-like acidic hydroxyl groups.

DESCRIPTION OF THE PREFERRED EMBODIMENTS

Ester Compound

The polymerizable fluorinated ester compound of the invention has the general formula (1) or (2).

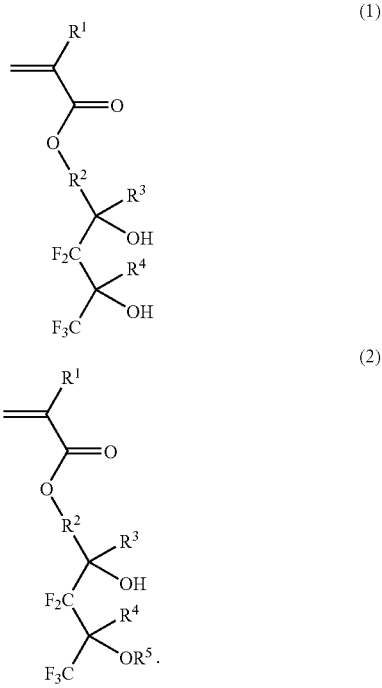

Herein $R^1$ is hydrogen, methyl or trifluoromethyl. $R^2$ is a straight, branched or cyclic, divalent hydrocarbon group of 1 to 15 carbon atoms. $R^3$ is hydrogen or a straight, branched or cyclic, monovalent hydrocarbon group of 1 to 15 carbon atoms. Alternatively, $R^2$ and $R^3$, taken together, may form a ring with the carbon atom to which they are attached. $R^4$ is hydrogen, hydroxyl or a straight, branched or cyclic, monovalent hydrocarbon group of 1 to 15 carbon atoms. $R^5$ is an acid labile group.

More particularly, $R^1$ is a hydrogen atom, methyl group or trifluoromethyl group.

$R^2$ is a straight, branched or cyclic, divalent $C_1$–$C_{15}$ hydrocarbon group. Exemplary divalent hydrocarbon groups are obtained by substituting a single bond for one hydrogen atom on monovalent hydrocarbon groups, examples of which include straight, branched or cyclic alkyl groups such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo

[2.2.2]octylmethyl, bicyclo[2.2.2]octylethyl, bicyclo[2.2.2] octylbutyl, methylbicyclo[2.2.2]octylmethyl, ethylbicyclo [2.2.2]octylmethyl, ethylbicyclo[2.2.2]octylethyl, tricyclo [5.2.1.0$^{2,6}$]decyl, tricyclo[5.2.1.0$^{2,6}$]decylmethyl, tricyclo [5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo [5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo [4.4.0.1$^{2,5}$.1$^{7,10}$]dodecylethyl, tetracyclo[4.4.0.1$^{2,5}$.1$^{7,10}$] dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, and ethyltetracyclo[4.4.0.1$^{2,5}$.1$^{7,10}$]dodecylethyl; aryl groups such as phenyl, tolyl, naphthyl, anthryl, and phenanthryl; and aralkyl groups such as benzyl, diphenylmethyl and phenethyl. Some of the hydrogen atoms on the foregoing groups may be replaced by halogen atoms, alkyl, aryl, alkoxy, alkoxycarbonyl or oxo groups. Of these, divalent hydrocarbon groups containing $C_5$–$C_{12}$ cycloaliphatic hydrocarbon, for example, divalent hydrocarbon groups containing cyclopentane, cyclohexane, bicyclo[2.2.1]heptane, bicyclo [2.2.2]octane, tricyclo[5.2.1.0$^{2,6}$]decane, adamantane, tetracyclo[4.4.0.1$^{2,5}$.1$^{7,10}$]dodecane or the like, and divalent hydrocarbon groups represented by —$(CH_2)_n$— wherein n is an integer of 1 to 8 are preferred for resist characteristics and ease of preparation.

$R^3$ is hydrogen or a straight, branched or cyclic, monovalent $C_1$–$C_{15}$ hydrocarbon group. Examples of the straight, branched or cyclic, monovalent $C_1$–$C_{15}$ hydrocarbon group include straight, branched or cyclic alkyl groups such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1] heptylmethyl, bicyclo[2.2.1]heptylethyl, bicyclo[2.2.1]heptylbutyl, methylbicyclo[2.2.1]heptylmethyl, ethylbicyclo [2.2.1]heptylmethyl, ethylbicyclo[2.2.1]heptylethyl, bicyclo [2.2.2]octyl, bicyclo[2.2.2]octylmethyl, bicyclo[2.2.2] octylethyl, bicyclo[2.2.2]octylbutyl, methylbicyclo[2.2.2] octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo [4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$] dodecylmethyl, ethyltetracyclo[4.4.0.1$^{2,5}$.1$^{7,10}$] dodecylmethyl, and ethyltetracyclo[4.4.0.1$^{2,5}$.1$^{7,10}$] dodecylethyl; aryl groups such as phenyl, tolyl, naphthyl, anthryl, and phenanthryl; and aralkyl groups such as benzyl, diphenylmethyl and phenethyl. Some of the hydrogen atoms on the foregoing groups may be replaced by halogen atoms, alkyl, aryl, alkoxy, alkoxycarbonyl or oxo groups. Of these, preferred are lower alkyl groups such as methyl, ethyl, propyl and isopropyl, and monovalent hydrocarbon groups containing $C_5$–$C_{12}$ cycloaliphatic hydrocarbon, for example, monovalent hydrocarbon groups containing cyclopentane, cyclohexane, bicyclo[2.2.1]heptane, bicyclo[2.2.2]octane, tricyclo[5.2.1.0$^{2,6}$]decane, adamantane, tetracyclo [4.4.0.1$^{2,5}$.1$^{7,10}$]dodecane or the like.

Alternatively, $R^2$ and $R^3$ may bond together to form a ring with the carbon atom to which they are attached. Examples of the fluorinated ester compound wherein $R^2$ and $R^3$ form a ring include structures of the general formulae (7) and (8).

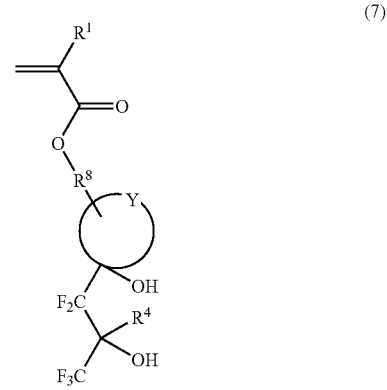

(7)

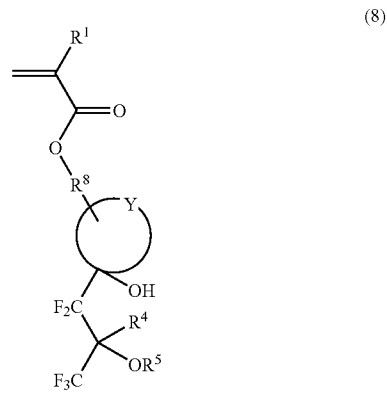

(8)

Herein $R^1$ is hydrogen, methyl or trifluoromethyl, $R^4$ is hydrogen, hydroxyl or a straight, branched or cyclic, monovalent $C_1$–$C_{15}$ hydrocarbon group, $R^5$ is an acid labile group, and $R^8$ is a single bond or —$(CH_2)_m$— wherein m is an integer of 1 to 3. The ring:

stands for a $C_5$–$C_{12}$ cycloaliphatic hydrocarbon.

Examples of the $C_5$–$C_{12}$ cycloaliphatic hydrocarbon formed herein include cyclopentane, cyclohexane, bicyclo [2.2.1]heptane, bicyclo[2.2.2]octane, tricyclo[5.2.1.0$^{2,6}$]decane, adamantane, tetracyclo[4.4.0.1$^{2,5}$.1$^{7,10}$]dodecane or the like. Some of the hydrogen atoms on these cycloaliphatic hydrocarbons may be replaced by halogen atoms, alkyl, aryl, alkoxy, alkoxycarbonyl, oxo or analogous groups.

$R^4$ is a hydrogen atom, a hydroxyl group or a straight, branched or cyclic, monovalent $C_1$–$C_{15}$ hydrocarbon residue. Examples of the monovalent $C_1$–$C_{15}$ hydrocarbon group are as exemplified above for $R^2$ and $R^3$. Of these, hydrogen, hydroxyl and methyl are most preferred.

$R^5$ is an acid labile group. The acid labile group may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

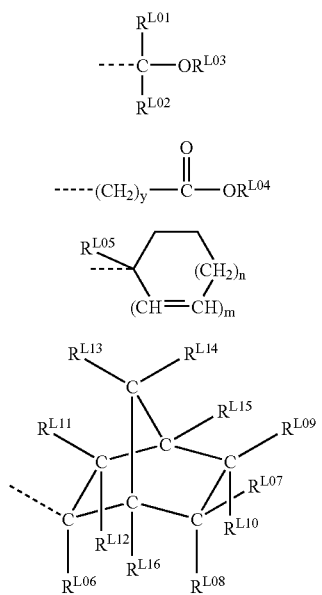

In these formulae and throughout the specification, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, n-propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like. Illustrative examples are the substituted alkyl groups shown below.

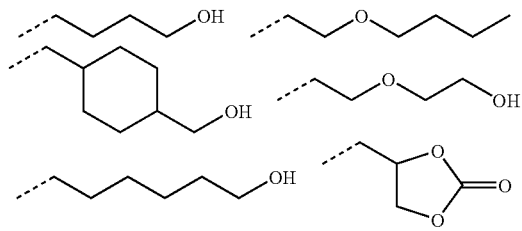

A pair of $R^{L01}$ and $R^{L02}$, $R^{L01}$ and $R^{L03}$, or $R^{L02}$ and $R^{L03}$ may form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

$R^{L05}$ is a monovalent hydrocarbon group of 1 to 8 carbon atoms or a substituted or unsubstituted aryl group of 6 to 20 carbon atoms. Examples of the monovalent hydrocarbon group include straight, branched or cyclic alkyl groups such as methyl, ethyl, n-propyl, isopropyl, n-butyl, sec-butyl, tert-butyl, tert-amyl, n-pentyl, n-hexyl, cyclopentyl, and cyclohexyl, and substituted groups in which some hydrogen atoms on the foregoing groups are substituted with hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2 m+n is equal to 2 or 3.

$R^{L06}$ is a monovalent hydrocarbon group of 1 to 8 carbon atoms or a substituted or unsubstituted aryl group of 6 to 20 carbon atoms. Examples of these groups are the same as exemplified for $R^{L05}$.

$R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, n-propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted ones of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$–$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

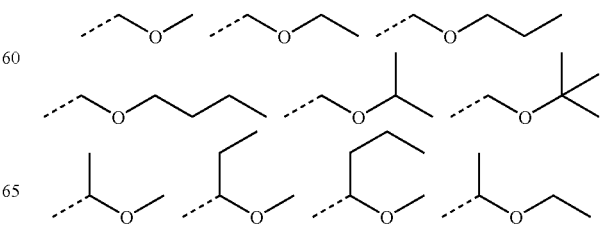

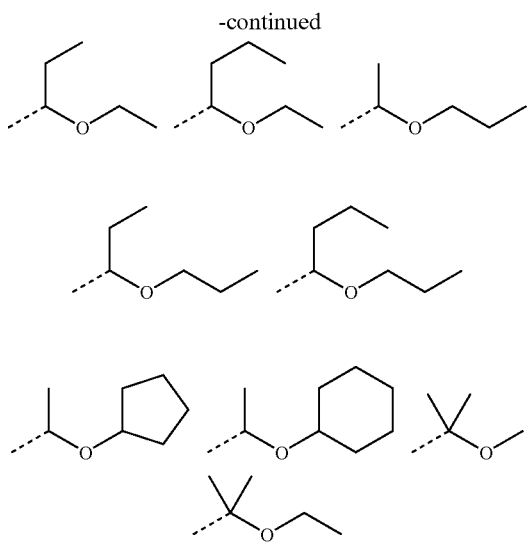

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

In formulae (1) and (2), $R^2$, $R^3$, $R^4$ and $R^5$ may be selected as appropriate in consideration of the transparency, etch resistance, solubility and other performance factors of a resist resin resulting from polymerization of the fluorinated ester compound.

Depending on the type and structure of $R^2$, $R^3$, $R^4$ and $R^5$, carbon atoms constituting the molecule can be asymmetric, and there can exist enantiomers and diastereomers. Each of formulae (1) and (2) collectively represents all such stereoisomers. Such stereoisomers may be included alone or in admixture.

Illustrative examples of the fluorinated ester compound having formula (1) are given below, but are not limited thereto.

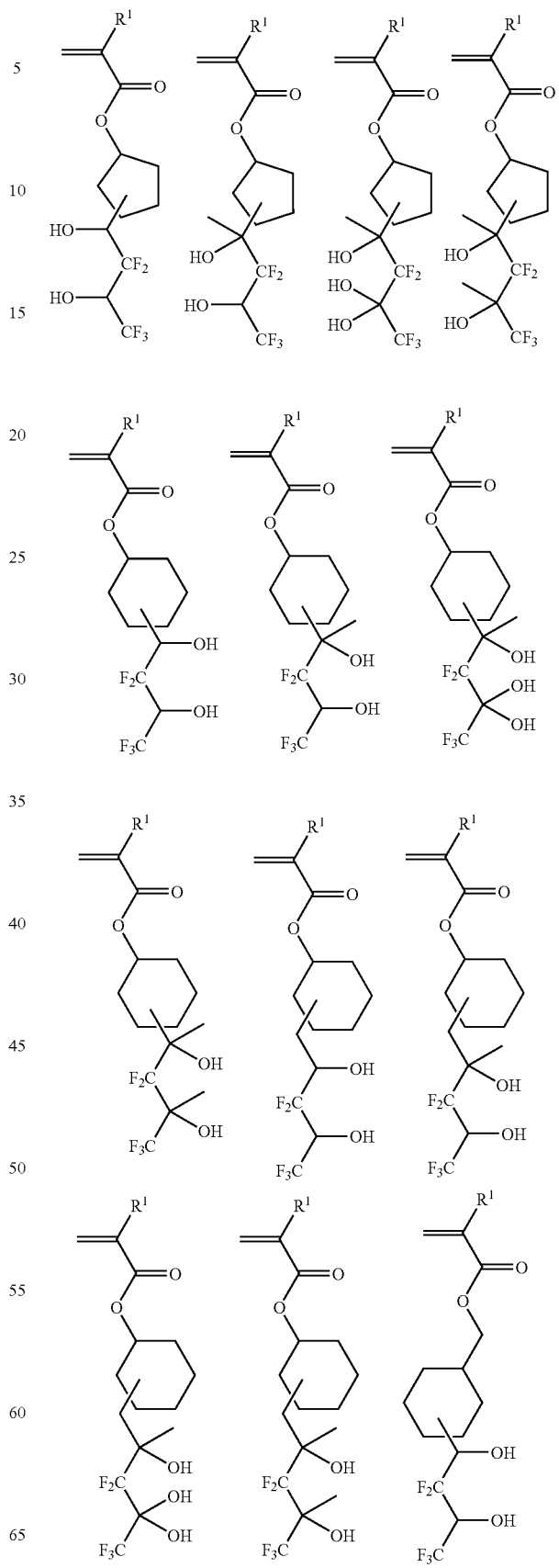

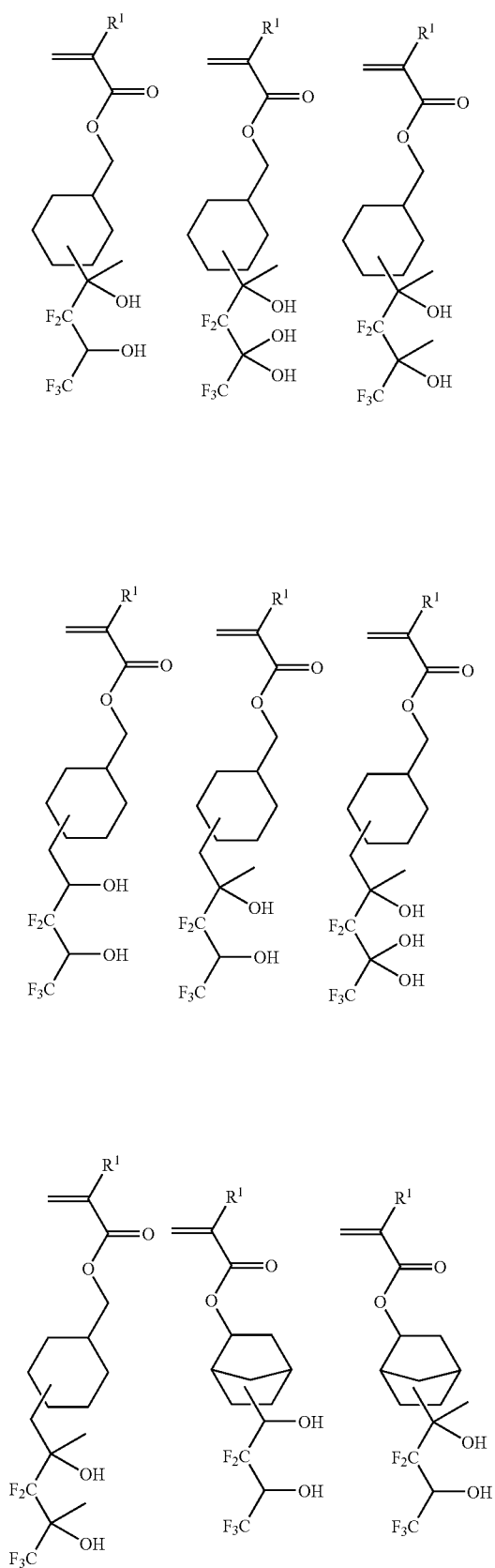

-continued
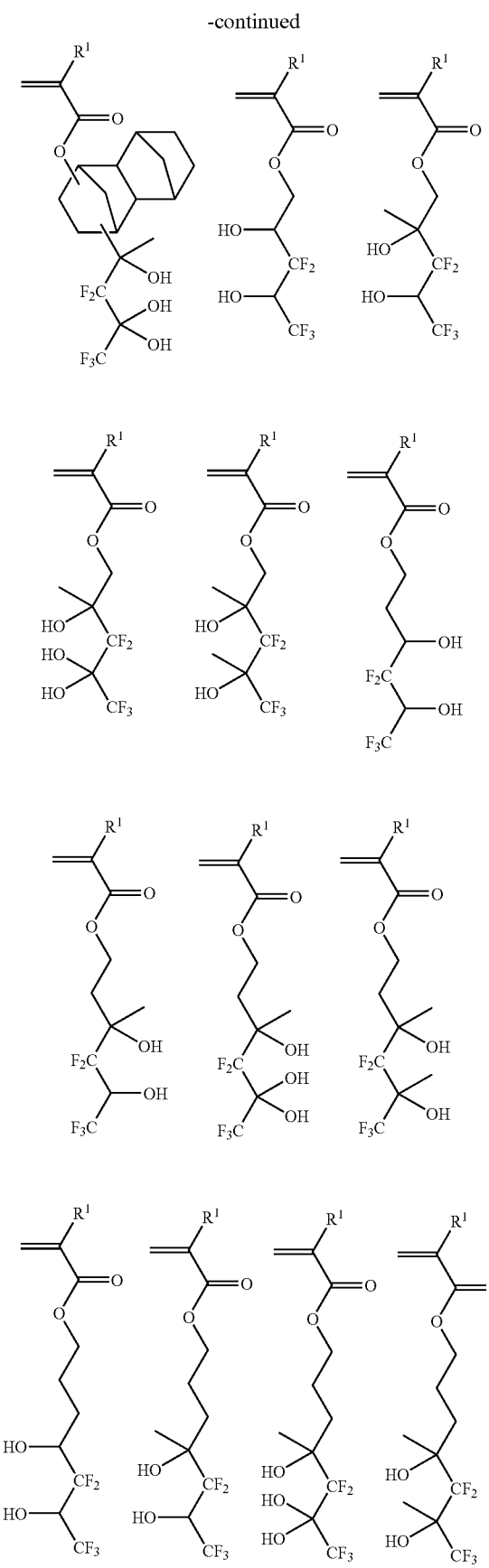
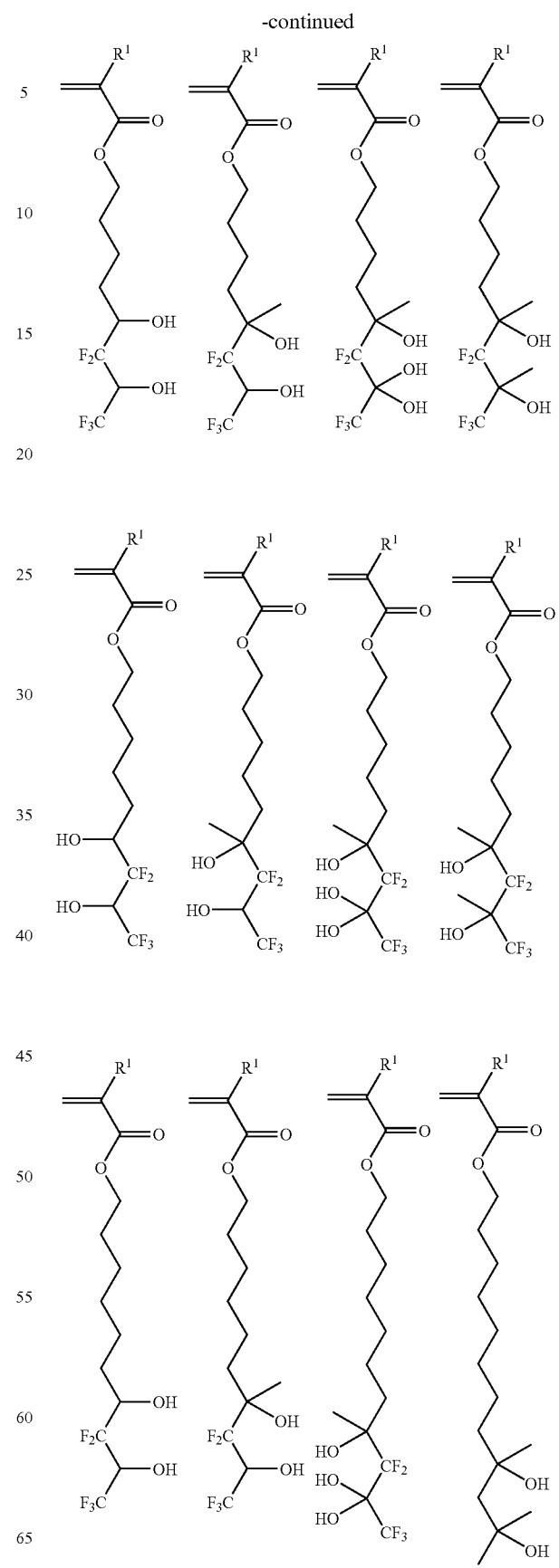

-continued
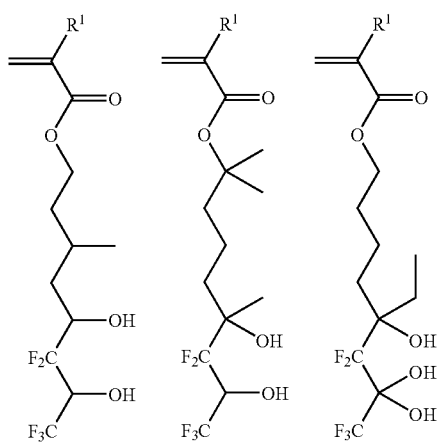
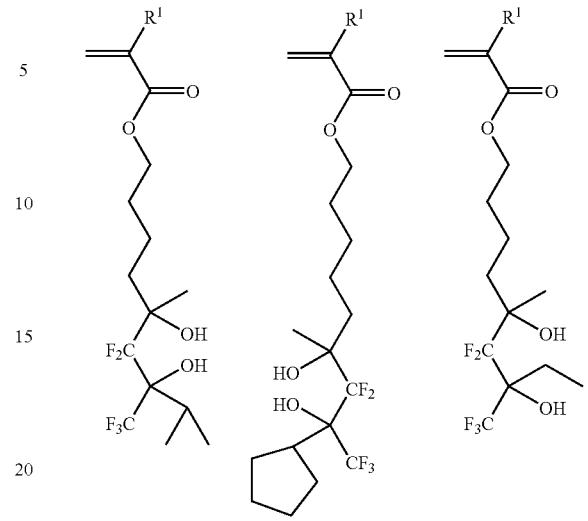
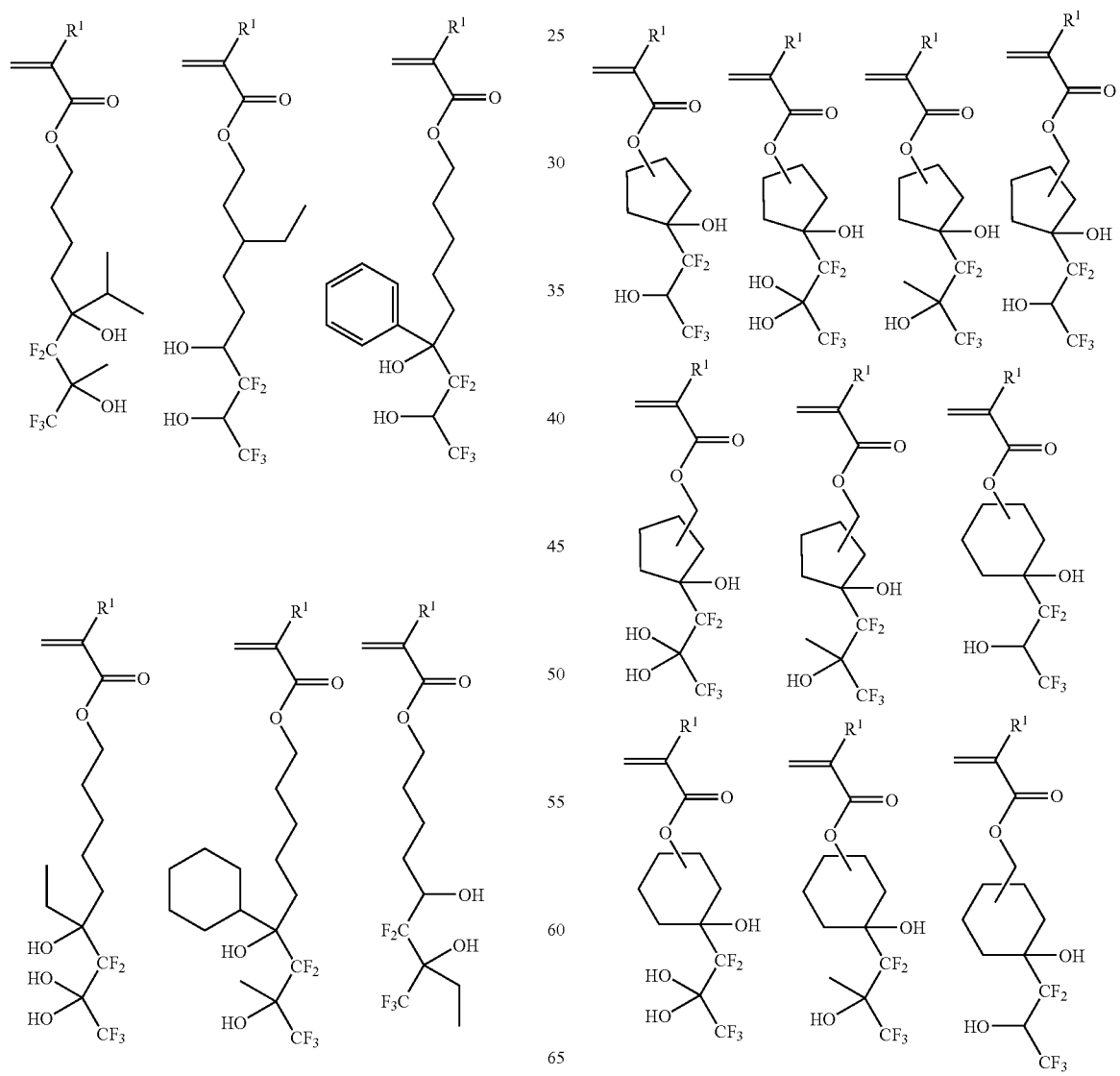

-continued
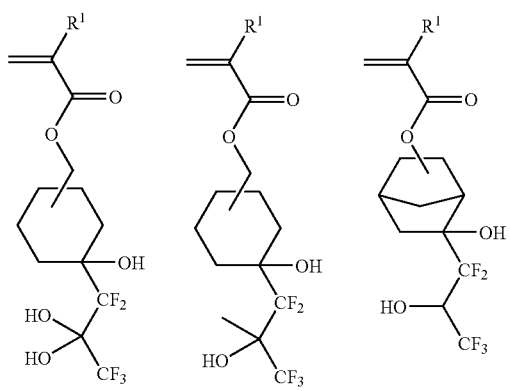
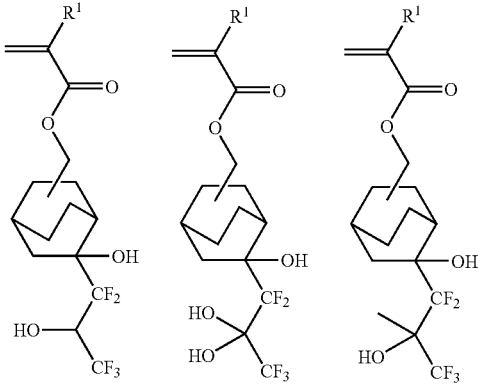
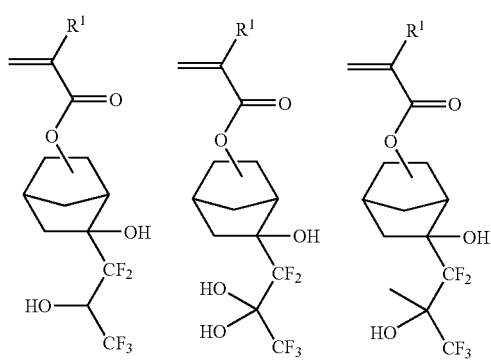
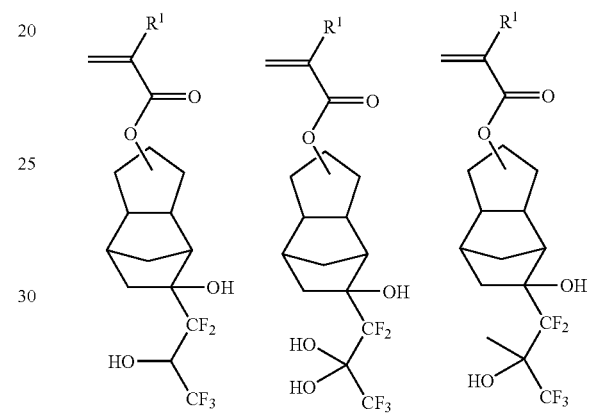
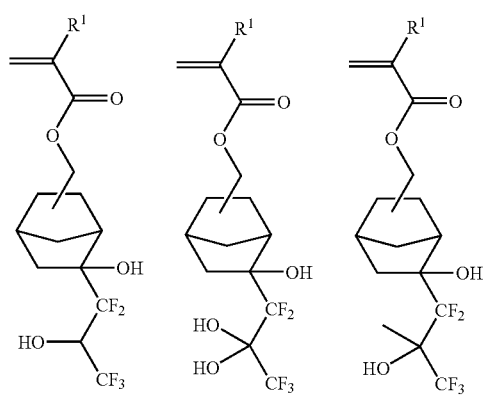
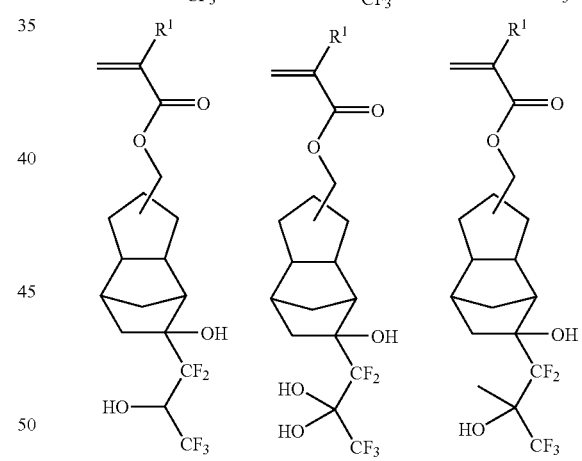
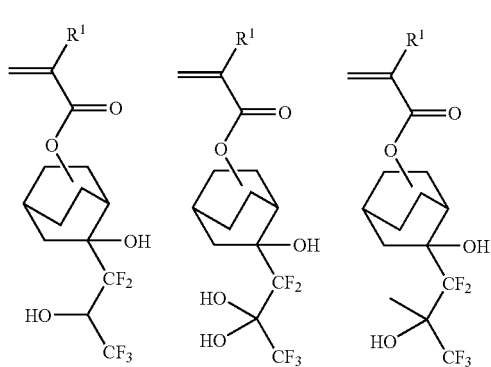
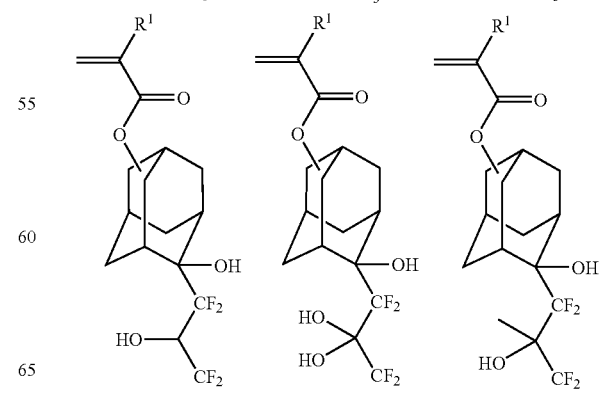

-continued

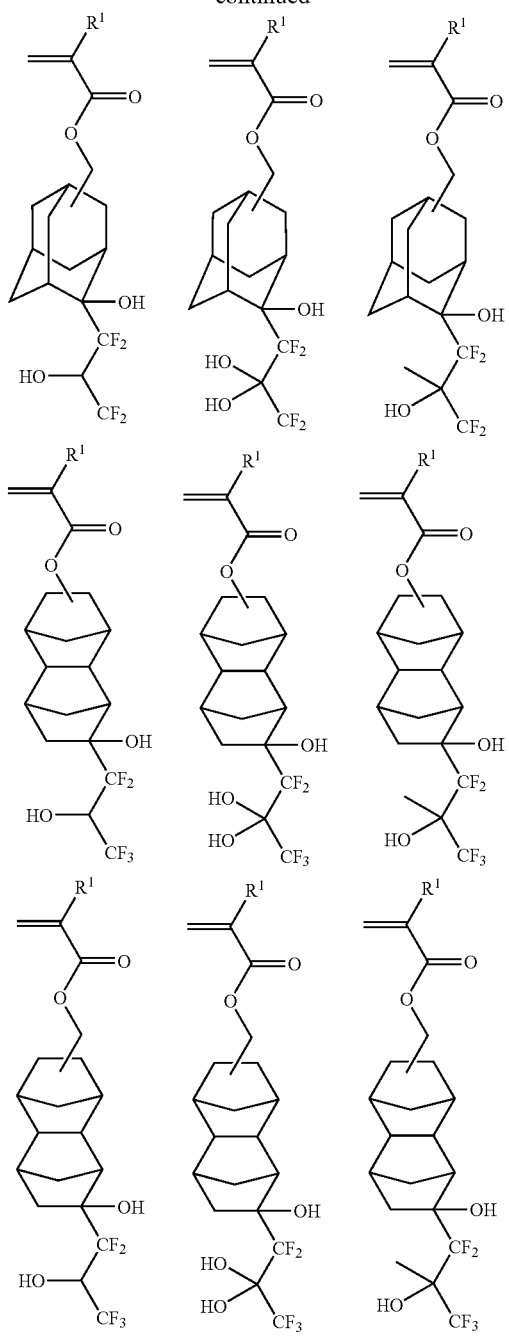

Herein, $R^1$ is hydrogen, methyl or trifluoromethyl.

Illustrative examples of the fluorinated ester compound having formula (2) include the exemplary compounds of formula (1) wherein a hydroxyl group is protected with an acid labile group $R^5$.

Preparation Method

The methods of preparing the polymerizable fluorinated ester compounds of the invention are described.

In a first embodiment, the polymerizable fluorinated ester compound having the general formula (1) is prepared by reacting a carbonyl compound having the general formula (3) with 1,1,3,3,3-pentafluoro-2-propenyl oxide to form a compound having the general formula (4), and reacting the compound having formula (4) with a compound $R^4$-Z to form the target polymerizable fluorinated ester compound having formula (1).

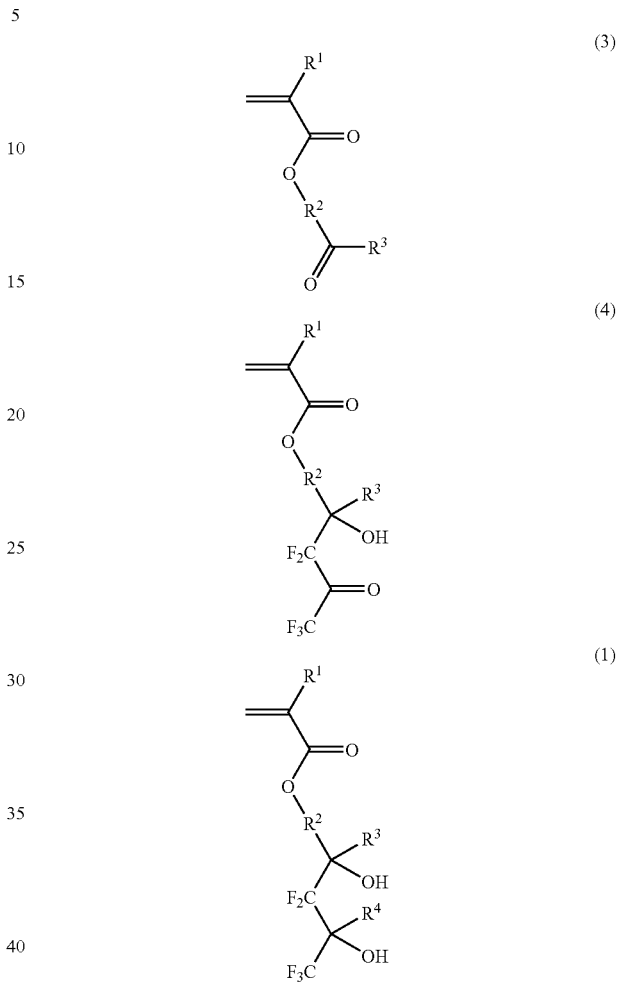

Herein $R^1$ is hydrogen, methyl or trifluoromethyl, $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached, $R^4$ is hydrogen, hydroxyl or a straight, branched or cyclic, monovalent $C_1$–$C_{15}$ hydrocarbon group, and Z is such a monovalent group that $R^4$-Z provides a $R^4$ anion equivalent.

The first stage is to react a carbonyl compound (3) with 1,1,3,3,3-pentafluoro-2-propenyl oxide. One reactant, 1,1,3,3,3-pentafluoro-2-propenyl oxide can be readily synthesized from 1,1,1,3,3,3-hexafluoro-2-propanol which is commercially available in plenty, has a melting point of −4° C. to −2° C. and a boiling point of 59–60° C., and is liquid at room temperature and easy to handle. See T. Nakai et al., Tetrahedron Letters, Vol. 29, p. 4119, 1988 and T. Nakai et al., Organic Syntheses, Vol. 76, p. 151, 1998. In this nucleophilic addition reaction of fluoro-enolate to carbonyl compound, various aldehydes (where $R^3$ is hydrogen) and ketones (where $R^3$ is a straight, branched or cyclic monovalent $C_1$–$C_{15}$ hydrocarbon group) may be used as the carbonyl compound (3).

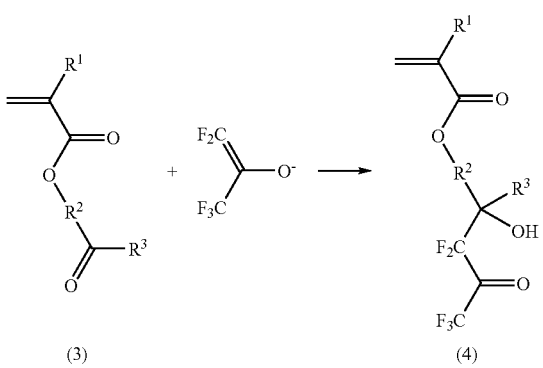

(3)        (4)

Herein $R^1$ is hydrogen, methyl or trifluoromethyl, $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached.

The reaction is generally carried out in an atmosphere of inert gas such as nitrogen or argon and in a solvent. Preferred examples of the solvent used include ethers such as diethyl ether, dibutyl ether, diethylene glycol diethyl ether, diethylene glycol dimethyl ether, tetrahydrofuran, and 1,4-dioxane. A choice may also be made among hydrocarbons such as hexane, heptane, benzene, toluene, xylene and cumene, nitriles such as acetonitrile, and aprotic polar solvents such as N,N-dimethylformamide and hexamethylphosphoric triamide, alone or in admixture of two or more. The reaction temperature is preferably from −50° C. to approximately the boiling point of the solvent, and more preferably from −20° C. to 100° C. It is desirable from the yield standpoint to force the reaction to completion while monitoring the reaction by gas chromatography (GC) or thin layer chromatography (TLC), although the reaction time is usually about 0.1 to about 250 hours. At the end of reaction, the compound (4) is obtained by a conventional aqueous work-up procedure.

The keto-alcohol compound (4) resulting from the reaction is sometimes obtained as a hydrate having the general formula (8) as a result of water adding to the carbonyl group through work-up with water or the like, or an oxetane hemi-acetal compound having the general formula (9) as a result of the hydroxyl group within the molecule adding to the carbonyl group within the molecule, or a mixture of these two or three.

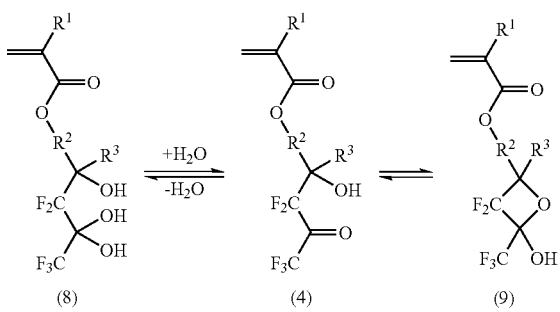

(8)        (4)        (9)

Herein $R^1$ is hydrogen, methyl or trifluoromethyl, $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached.

Sometimes the mixture of these compounds is ready for use in the subsequent reaction. Otherwise, simple dehydration operation is carried out to bias the equilibrium toward the keto-alcohol compound prior to the subsequent reaction. Thus for convenience of description, these compounds are typically represented by keto-alcohol compound, formula (4). Since the keto-alcohol compounds have asymmetric carbon atoms within the molecule, there can exist enantiomers and diastereomers. Each of formulae (4), (8) and (9) collectively represents all such stereoisomers. Such stereoisomers may be used alone or as a mixture.

The second stage is to react the carbonyl compound (4) with a compound $R^4$-Z.

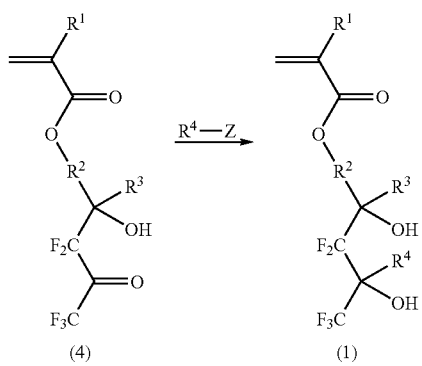

(4)        (1)

Herein $R^1$ is hydrogen, methyl or trifluoromethyl, $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached, $R^4$ is hydrogen, hydroxyl or a straight, branched or cyclic, monovalent $C_1$–$C_{15}$ hydrocarbon group, and Z is such a monovalent group that $R^4$-Z provides a $R^4$ anion equivalent.

This reaction is carried out by combining the fluoroketone compound (4) with a compound $R^4$-Z in the presence or absence of a solvent. $R^4$-Z represents a $R^4$ anion equivalent and may be suitably selected depending on the desired type of $R^4$. Illustrative examples include water (where $R^4$ is a hydroxyl group); alkyl metals (where $R^4$ is a hydrocarbon group) such as methyllithium, butyllithium, phenyllithium, methylmagnesium chloride, ethylmagnesium chloride, and phenylmagnesium chloride; metal hydrides (where $R^4$ is hydrogen) such as sodium hydride, potassium hydride, calcium hydride, aluminum hydride (or alane), boron hydride (or boran), and diisobutylaluminum hydride; and metal hydride complexes such as sodium borohydride and lithium aluminum hydride or alkyl or alkoxy derivatives thereof (where $R^4$ is hydrogen). The amount of $R^4$-Z used is from 1 mole to large excess per mole of the carbonyl compound (4). It is noted that an unprotected hydroxyl group is present in the reaction substrate (4), and if it consumes 1 mole of $R^4$-Z, the amount of $R^4$-Z used is preferably at least 2 moles. It is also sometimes necessary to adjust the amount of $R^4$-Z used in order to avoid side reaction with the ester carbonyl group within the molecule. Where the reaction is carried out in a solvent, examples of the solvent which can be used include water, alcohols such as methanol, ethanol, n-propyl alcohol and isopropyl alcohol, hydrocarbons such as hexane, heptane, benzene, toluene, xylene and cumene, ethers such as diethyl ether, dibutyl ether, diethylene glycol diethyl ether, diethylene glycol dimethyl ether, tetrahydrofuran and 1,4-dioxane, nitriles such as acetonitrile, ketones such as acetone, esters such as ethyl acetate, and aprotic polar solvents such as such as N,N-dimethylformamide and hexamethylphosphoric triamide. Any appropriate one or mixture may be selected from these solvents. An appropriate reaction temperature may be selected depending on the type and amount of $R^4$-Z used, although it is preferably from −50° C. to approximately the boiling point of the solvent, and more preferably from −20° C. to 100° C. It is desirable from the yield standpoint to force the reaction to completion while monitoring the reaction by gas chromatography (GC) or thin layer chromatography (TLC), although the reaction time is usually about 0.1 to about 50 hours. At the end of reaction, the target compound (1) is obtained by a conventional aqueous work-up step.

If necessary, the target compound (1) is purified by any conventional technique such as recrystallization, chromatography or distillation.

In a second embodiment, the polymerizable fluorinated ester compound having the general formula (1) is prepared by acylating an alcohol compound having the general formula (5).

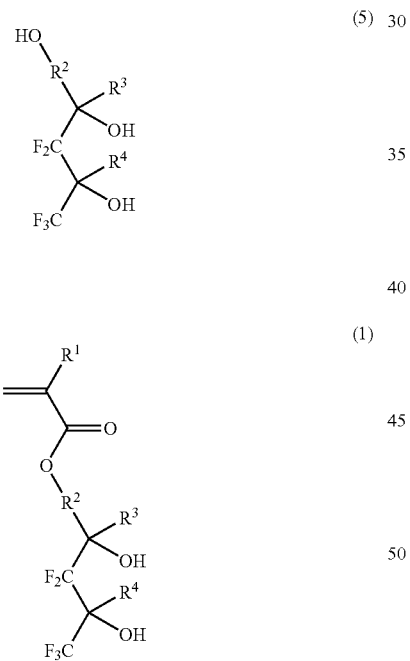

Herein $R^1$ is hydrogen, methyl or trifluoromethyl, $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached, and $R^4$ is hydrogen, hydroxyl or a straight, branched or cyclic, monovalent $C_1$–$C_{15}$ hydrocarbon group.

Although the synthesis process widely varies with the type of substituents $R^2$, $R^3$ and $R^4$, the starting reactant, triol compound (5) can be synthesized, for example, according to the scheme shown below, using as a key reaction the addition reaction of 1,1,3,3,3-pentafluoro-2-propenyl oxide to the carbonyl compound described in the first embodiment.

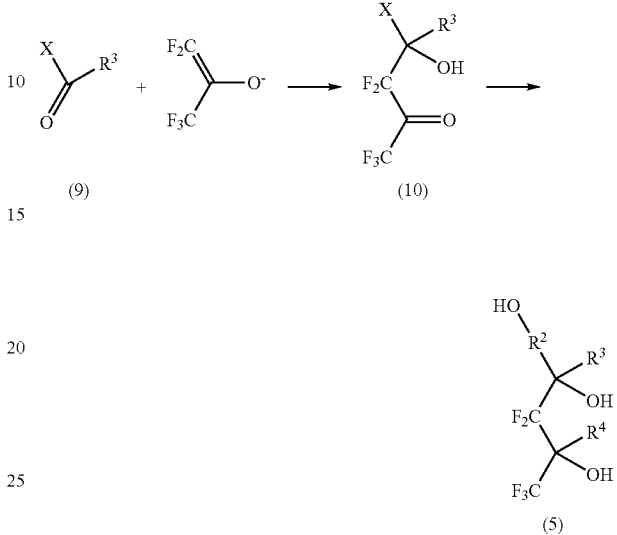

Herein $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached, $R^4$ is hydrogen, hydroxyl or a straight, branched or cyclic, monovalent $C_1$–$C_{15}$ hydrocarbon group, and X is a group which can be converted into $R^2$—OH.

Specifically, the triol compound (5) can be synthesized by a route involving the steps of reacting the carbonyl compound (9) with 1,1,3,3,3-pentafluoro-2-propenyl oxide to form a fluoroketone compound (10), introducing a substituent group $R^4$, and converting the substituent group X to $R^2$—OH. The substituent group X may be selected from a wide range, typically those groups containing a protected hydroxyl group which can be converted into $R^2$—OH through deprotection, and those groups containing an aldehyde (formyl) or ester (alkoxycarbonyl) group which can be converted into $R^2$—OH through reduction or alkylation reaction. A proper choice of substituent group and reaction conditions enables to effect the introduction of a substituent group $R^4$ and the conversion of the substituent group X to $R^2$—OH at the same time.

For the acylation of triol compound (5) to ester compound (1), well-known ester preparation processes including reaction with acylating agents, reaction with carboxylic acids and transesterification are applicable.

Since the triol compound (5) has plural hydroxyl groups which can be acylated, the position selectivity of reaction is a problem. That is, there is a possibility that a position isomer having the general formula (1') or (1") form in addition to the desired compound (1).

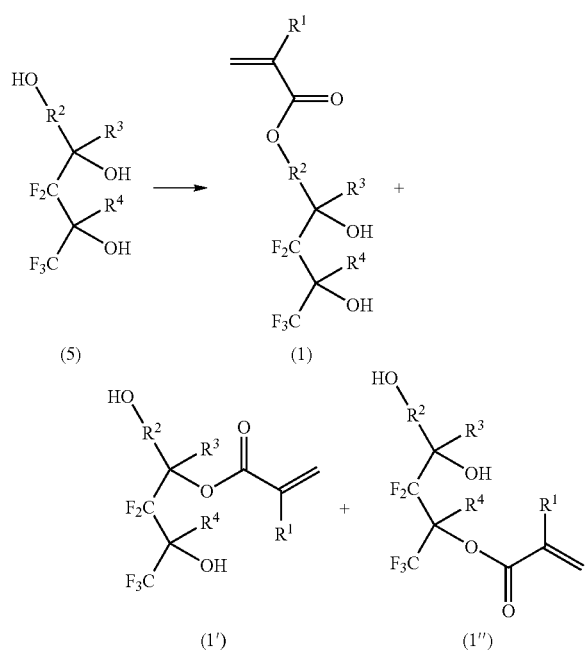

(5) (1)

(1') (1")

Some triol compounds (5) contain hydroxyl groups which are distinguished by steric hindrance so that the desired position to be acylated is less hindered in space. Some other triol compounds (5) contain hydroxyl groups having different degrees of acidity, despite a similar degree of steric hindrance, allowing the desired compound (1) to be selectively produced therefrom by properly controlling reaction conditions. In these cases, the triol compound (5) can be used as the reaction substrate without protecting any hydroxyl groups, and subjected to acylating reaction to be described below. This route is of industrial great worth because it is short as compared with a route via protection and deprotection steps. Otherwise, the target compound and its position isomer (1') or (1") can be separated by purification to be described below while they can be employed as a mixture in the subsequent step like resin preparation. The ratio of isomers is arbitrary although the ratio of desired compound (1) to isomer is preferably at least 0.3, more preferably at least 0.5.

In the reaction using the acylating agent, the reactant or triol compound (5), an acylating agent, and a base are sequentially or simultaneously fed to a solvent whereupon reaction takes place. Examples of the solvent used herein include chlorinated solvents such as methylene chloride, chloroform and trichloroethylene, hydrocarbons such as hexane, heptane, benzene, toluene, xylene and cumene, ethers such as dibutyl ether, diethylene glycol diethyl ether, diethylene glycol dimethyl ether, tetrahydrofuran and 1,4-dioxane, nitriles such as acetonitrile, ketones such as acetone and 2-butanone, esters such as ethyl acetate and n-butyl acetate, and aprotic polar solvents such as N,N-dimethylformamide, dimethyl sulfoxide and hexamethylphosphoric triamide, alone or as a mixture. Examples of the acylating agent include acid halides such as acryloyl chloride, methacryloyl chloride, acryloyl bromide, methacryloyl bromide, and α-trifluoromethylacryloyl chloride; and acid anhydrides such as acrylic anhydride, methacrylic anhydride, α-trifluoromethylacrylic anhydride, acrylic/trifluoroacetic mixed anhydride, methacrylic/trifluoroacetic mixed anhydride, a-trifluoromethylacrylic/trifluoroacetic mixed anhydride, acrylic/p-nitrobenzoic mixed anhydride, methacrylic/p-nitrobenzoic mixed anhydride, acrylic/ethyl carbonic mixed anhydride, and methacrylic/ethyl carbonic mixed anhydride. Suitable bases include triethylamine, diisopropylethylamine, N,N-dimethylaniline, pyridine, and 4-dimethylaminopyridine. An appropriate reaction temperature may be selected depending on the type of acylating agent used and other reaction conditions, although it is preferably from −50° C. to approximately the boiling point of the solvent, and more preferably from −20° C. to room temperature. The amount of the acylating agent used depends on its structure and is generally in the range of 1 to 40 moles, preferably 1 to 5 moles per mole of triol compound (5).

In the course of reaction using the acylating agent, a position isomer in which the hydroxyl group other than the desired one on triol compound (5) is acylated forms as a main product at the initial phase of reaction, but as the reaction continues longer, gradual isomerization into the target compound (1) may take place. It accounts for this phenomenon that under basic conditions, the hydroxyl group having a higher acidity (more susceptible to deprotonation by base) is acylated at the initial phase so that the position isomer is likely to form as a kinetic product, but the target compound (1) which is believed to be stable as a thermodynamic product in the system accumulates over a long term of reaction.

The reaction with carboxylic acids is a dehydrating reaction from a corresponding carboxylic acid, i.e., any of acrylic acid, methacrylic acid and α-trifluoromethylacrylic acid and the reactant, triol compound (5), which is generally performed in the presence of an acid catalyst. An appropriate amount of carboxylic acid used is 1 to 40 moles, more preferably 1 to 5 moles per mole of the triol compound (5), though it depends on the structure of acid. Examples of the acid catalyst include inorganic acids such as hydrochloric acid, hydrobromic acid, sulfuric acid, and nitric acid, and organic acids such as oxalic acid, trifluoroacetic acid, methanesulfonic acid, benzenesulfonic acid, and p-toluenesulfonic acid, alone or as a mixture of any. An appropriate amount of the acid catalyst used is 0.001 to 1 mole, more preferably 0.01 to 0.05 mole per mole of the triol compound (5). Examples of the solvent used are as exemplified above for the reaction with the acylating agent. The reaction temperature is preferably from −50° C. to approximately the boiling point of the solvent. The reaction may also be performed in a solvent comprising a hydrocarbon such as hexane, heptane, benzene, toluene, xylene or cumene, while azeotroping the formed water out of the system. In this embodiment, the water may be distilled off while refluxing under atmospheric pressure, or the water be distilled off under reduced pressure at a lower temperature than the boiling point.

The transesterification is implemented by reacting the reactant, triol compound (5) with a corresponding carboxylic acid ester, i.e., any of acrylate, methacrylate and a-trifluoromethylacrylate in the presence of a catalyst and removing the alcohol formed. The carboxylic acid esters used are preferably primary alkyl esters. Inter alia, methyl, ethyl and n-propyl esters are preferred because of low cost and smooth progress of reaction. An appropriate amount of carboxylic acid ester used is 1 to 40 moles, more preferably 1 to 5 moles per mole of the triol compound (5), though it depends on the structure of ester. Examples of the catalyst include inorganic acids such as hydrochloric acid, hydrobromic acid, sulfuric acid, and nitric acid, organic acids such as oxalic acid, trifluoroacetic acid, methanesulfonic acid, benzenesulfonic acid, and p-toluenesulfonic acid, bases such as sodium methoxide, sodium ethoxide, potassium t-butoxide, and 4-dimethylaminopyridine, and salts such as sodium cyanide, potassium cyanide, sodium acetate, potassium acetate, calcium acetate, tin acetate, aluminum acetate, aluminum acetoacetate, alumina, and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium (IV) ethoxide, titanium(IV) isopropoxide, and titanium(IV) oxide, alone or as a mixture of any. An appropriate amount of the catalyst used is 0.001 to 20 moles, more preferably 0.01 to 0.05 mole per mole of the triol compound (5). The reaction may be performed in a solventless system (the reagent, carboxylic acid ester itself may serve as a solvent), which is preferred in that extra operations such as concentration and solvent recovery are eliminated. A solvent may be used in a supplemental manner for the purpose of preventing polymerization of the target compound and the reagent. Examples of the solvent, if used, include hydrocarbons such as hexane, heptane, benzene, toluene, xylene and cumene, and ethers such as dibutyl ether, diethylene glycol diethyl ether, diethylene glycol dimethyl ether, tetrahydrofuran, and 1,4-dioxane, alone or as a mixture. An appropriate reaction temperature may be selected depending on the type of carboxylic acid ester used and other reaction conditions. Usually, the reaction is performed at elevated temperature. Better results are obtained when the reaction is performed at a temperature approximate to the boiling point of a low boiling point alcohol formed by transesterification reaction such as methanol, ethanol or 1-propanol, whereby the alcohol formed is distilled off during the reaction. The alcohol may be distilled off under reduced pressure at a lower temperature than the boiling point.

It is desired for higher yields that the time of acylating reaction is determined by monitoring the progress of reaction (including not only acylating reaction, but also isomerization) by GC or TLC. The reaction time is usually about 0.1 hour to about 240 hours. After the completion of reaction, the target fluorinated ester compound (1) is recovered from the reaction mixture by a conventional work-up procedure such as aqueous work-up and concentration.

If necessary, the compound (1) can be purified by any conventional technique such as recrystallization, chromatography or distillation. The target compound (1) and its position isomer (1') or (1") may be separated at this purifying stage as previously described. Alternatively, a mixture of compounds (1) and (1') or (1") may be used, without purification, in the subsequent step like resin preparation.

The polymerizable fluorinated ester compound having formula (2) can be prepared by protecting or blocking one of the hydroxyl groups on the polymerizable fluorinated ester compound having formula (1) with an acid labile group $R^5$.

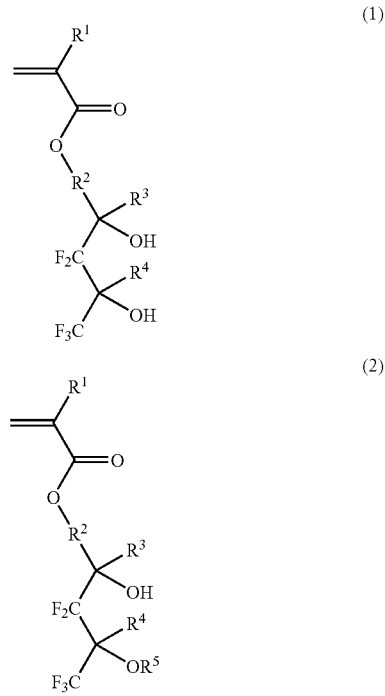

Herein $R^1$ is hydrogen, methyl or trifluoromethyl, $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached, $R^4$ is hydrogen, hydroxyl or a straight, branched or cyclic, monovalent $C_1$–$C_{15}$ hydrocarbon group, and $R^5$ is an acid labile group.

The reaction may be carried out by conventional processes. In the event of protection with acyl protective groups, for example, well-known ester preparation processes including reaction with acylating agents, reaction with carboxylic acids and transesterification are applicable, provided that suitable corresponding reactants are used. In the event of using ether protective groups, reaction with halides under basic conditions and addition reaction to unsaturated compounds under acidic conditions are typical. In the event of silyl protective groups, reaction with chlorosilanes under basic conditions is typical. These reactions are merely exemplary.

If necessary, the target compound (2) can be purified by any conventional technique such as recrystallization, chromatography or distillation. The target compound (2) has a possibility that depending on the type of $R^2$, $R^3$, $R^4$ and $R^5$, their root carbon atom becomes asymmetric carbon, which means the presence of enantiomers or diastereomers. The general formula (2) collectively represents all such stereoisomers. The stereoisomers may be used alone or as a mixture.

Polymer

Using the polymerizable fluorinated ester compounds having formula (1) or (2) thus obtained, polymers comprising recurring units having the general formula (1a) or (2a), which may be homopolymer or copolymers, can be prepared by customary techniques like radical polymerization, anion polymerization and cation polymerization. In forming copolymers, the ester compounds are copolymerized with another polymerizable monomer of at least one type.

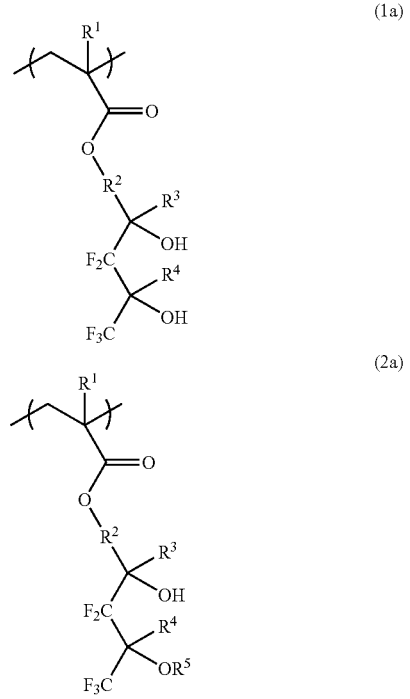

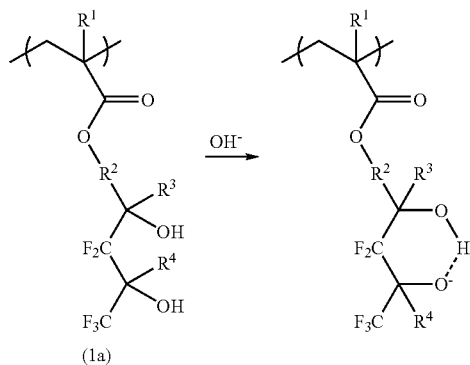

Herein $R^1$ is hydrogen, methyl or trifluoromethyl, $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached, $R^4$ is hydrogen, hydroxyl or a straight, branched or cyclic, monovalent $C_1$–$C_{15}$ hydrocarbon group, and the broken line denotes a hydrogen bond.

The polymer comprising recurring units having formula (2a) is decomposed under the action of an acid to form a partial structure having formula (1a), becoming an alkali soluble polymer.

In a further embodiment, a polymerizable ester compound having the general formula (6) is copolymerized to form a polymer comprising recurring units of one or more type having the general formula (6a).

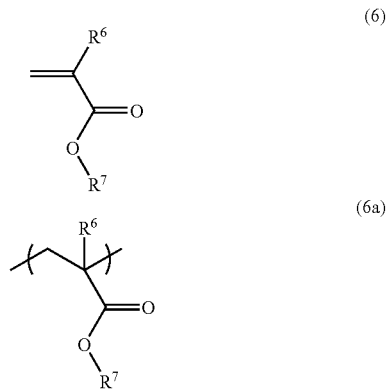

Herein $R^1$ is hydrogen, methyl or trifluoromethyl, $R^2$ is a straight, branched or cyclic, divalent $C_1$–$C_{15}$ hydrocarbon group, $R^3$ is hydrogen or a straight, branched or cyclic, monovalent $C_1$–$C_{15}$ hydrocarbon group, or $R^2$ and $R^3$, taken together, may form a ring with the carbon atom to which they are attached, $R^4$ is hydrogen, hydroxyl or a straight, branched or cyclic, monovalent $C_1$–$C_{15}$ hydrocarbon group, and $R^5$ is an acid labile group.

Polymers obtained through the polymerization of polymerizable fluorinated ester compounds according to the invention are fully transparent to radiation having a wavelength of up to 500 nm, especially up to 200 nm, and have good development properties due to the presence of phenol-like acidic hydroxyl groups, when used as the base resin in radiation-sensitive resist compositions. Examples of the radiation having a wavelength of up to 300 nm include ArF laser light (193 nm), $F_2$ laser light (157 nm), $Ar_2$ laser light (126 nm), and extreme ultraviolet radiation (EUV 13 nm).

The polymer comprising recurring units having the general formula (1a) exhibits an acidity like a phenolic hydroxyl group. This is believed due to the substitution of a plurality of fluorine atoms having electron withdrawing effect on adjacent carbon atoms. When one hydroxyl group is ionized, it can form a hydrogen bond with the hydrogen atom of an adjacent hydroxyl group, which is believed to contribute to the development of strong acidity.

Herein $R^6$ is hydrogen, methyl or trifluoromethyl, and $R^7$ is an acid labile group.

Examples of the acid labile group $R^7$ are as exemplified for $R^5$. $R^7$ may be the same or different from $R^5$. The polymer comprising recurring units having formula (6a) is decomposed under the action of an acid to generate a carboxylic acid, becoming an alkali soluble polymer.

In a still further embodiment, a polymerizable ester compound having the general formula (11) is copolymerized to form a polymer comprising recurring units of one or more type having the general formula (11a).

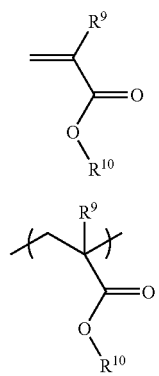

Herein $R^9$ is hydrogen, methyl or trifluoromethyl, and $R^{10}$ is a $C_2$–$C_{20}$ alkyl group containing at least one hydroxyl, carbonyl, ester (—COO—), ether (—O—) or cyano group.

Examples of the alkyl group represented by $R^{10}$ include, but are not limited to, 2-hydroxyethyl, 2-cyanoethyl, 3-hydroxy-1-adamantyl, 3,5-dihydroxy-1-adamantyl, hydroxynorbornan-2-yl, 3-cyano-1-adamantyl, cyanonorbornan-2-yl, 2-oxo-3-tetrahydrofuranyl, 2-oxo-4-tetrahydrofuranyl, 4-oxa-5-oxotricyclo[5.2.1.0$^{2,6}$]decyl, 2,6-norbornanecarbolacton-3-ylmethyl, 2,6-norbornanecarbolacton-5-yl, 3-methoxycarbonyl-2,6-norbornanecarbolacton-5-yl, 7-oxa-2,6-norbornanecarbolacton-5-yl, 7-oxa-2,3-norbornanecarbolacton-5-yl, 7-oxa-2,3-norbornanecarbolacton-6-yl, spiro[norbornane-2,4'-(2-oxotetrahydrofuran)]-5-yl, spiro[norbornane-2,4'-(2-oxotetrahydrofuran)]-6-yl. By adjusting the type and amount of recurring units having formula (11a), the hydrophilic/hydrophobic balance of the polymer can be optimized.

In addition to the recurring units having formulae (1a), (2a), (6a) and (11a), the inventive polymer may further comprise recurring units "q" derived from various compounds (monomers) having a polymerizable carbon-to-carbon double bond for improving the resist performance.

Suitable such monomers include α,β-unsaturated carboxylic acids and esters thereof, α,β-unsaturated nitriles, α,β-unsaturated lactones, unsaturated carboxylic anhydrides, maleimides, norbornene derivatives, tetracyclo[4.4.0.1$^{2,5}$.1$^{7,10}$]dodecene derivatives, allyl ethers, vinyl ethers, vinyl esters, and vinylsilanes.

More particularly, suitable α,β-unsaturated carboxylic acids include (meth)acrylic acid, α-trifluoromethylacrylic acid, etc.; suitable α,β-unsaturated carboxylic esters include alkyl esters of α,β-unsaturated carboxylic acids such as (meth)acrylic acid, crotonic acid, maleic acid, α-trifluoromethylacrylic acid, etc. (wherein exemplary alkyl groups are straight, branched or cyclic $C_1$–$C_{20}$ alkyl groups); a typical α,β-unsaturated nitrile is acrylonitrile; suitable α,β-unsaturated lactones include 5,6-dihydro-2H-pyran-2-one and 2(5H)-furanone; suitable unsaturated carboxylic anhydrides include maleic anhydride and itaconic anhydride; suitable maleimides include maleimide and N-substituted maleimides; suitable norbornene derivatives include norbornene, 5-norbornene-2-carboxylic acid and ester derivatives thereof; suitable tetracyclo[4.4.0.1$^{2,5}$.1$^{7,10}$]dodecene derivatives include tetracyclo[4.4.0.1$^{2,5}$.1$^{7,10}$]dodec-8-ene-3-carboxylic acid and ester derivatives thereof, 3-methyltetracyclo[4.4.0.1$^{2,5}$.1$^{7,10}$]dodec-8-ene-3-carboxylic acid and ester derivatives-thereof; a typical allyl ether is 2,5-dihydrofuran; suitable vinyl ethers include 2,3-dihydrofuran and 3,4-dihydro-2H-pyran; a typical vinyl ester is vinyl acetate; and suitable vinylsilanes include vinyltrimethylsilane, vinylpentamethylcyclotrisiloxane, vinylheptamethylcyclotetrasiloxane, vinylpentamethyldisiloxane, and bis(trimethylsilylmethyl)vinylmethylsilane.

Assume that UA stands for recurring units of formula (1a), UB stands for recurring units of formula (2a), UC stands for recurring units of formula (6a), UD stands for recurring units of formula (11a), and UE stands for recurring units "q", and U=UA+UB+UC+UD+UE. These parameters, as expressed in molar ratio, should preferably satisfy:

$0 \leq UA/U \leq 0.8$, especially $0 \leq UA/U \leq 0.5$,
$0 \leq UB/U \leq 0.8$, especially $0 \leq UB/U \leq 0.5$,
$0 \leq UC/U < 0.8$, especially $0.2 \leq UC/U < 0.6$,
$0.1 \leq UD/U \leq 0.8$, especially $0.2 \leq UD/U \leq 0.7$, and
$0.1 \leq UE/U \leq 0.8$, especially $0.2 \leq UE/U \leq 0.5$.

UA and UB are not equal to 0 at the same time, and satisfy $0<(UA+UB)/U \leq 0.8$, more preferably $0.01 \leq (UA+UB)/U \leq 0.5$, and even more preferably $0.05 \leq (UA+UB)/U \leq 0.3$.

The polymer of the invention should preferably have a weight average molecular weight (Mw) of about 2,000 to about 100,000 as determined by gel permeation chromatography (GPC) versus polystyrene standards. With a Mw of less than 2,000, film formation and resolution may be poor whereas a Mw of more than 100,000 can compromise resolution.

Resist Composition

Advantageously, the polymer of the invention is used as a base resin in a resist composition, typically a positive resist composition, especially a chemically amplified positive resist composition. Therefore, the present invention in the fourth aspect provides a resist composition comprising the above-described polymer. The resist composition is typically comprised of (A) the above-described polymer as a base resin, (B) a photoacid generator, (C) an organic solvent, and optionally (D) a basic compound.

Component B

The photoacid generator (B) may be any compound capable of generating an acid upon exposure to high energy radiation having a wavelength of up to 300 nm or electron beams as long as a resist composition comprising the photoacid generator, the inventive polymer and an organic solvent can be a homogeneous solution which is effectively applicable to form a uniform film.

Examples of the photoacid generator which can be used herein include:

(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives,
(ix) sulfonate derivatives, and
(x) oxime sulfonates.

These photoacid generators are described in detail.
(i) Onium salts of formula (P1a-1), (P1a-2) or (P1b):

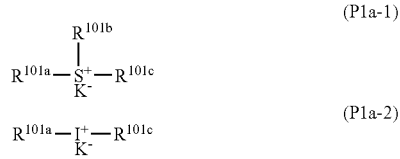

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

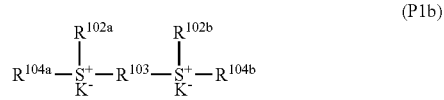

Herein, $R^{102a}$ and $R^{102b}$ independently represent straight, branched or cyclic alkyl groups of 1 to 8 carbon atoms. $R^{103}$ represents a straight, branched or cyclic alkylene group of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane Derivatives of Formula (P2)

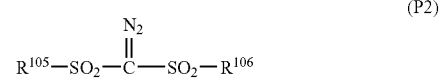

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

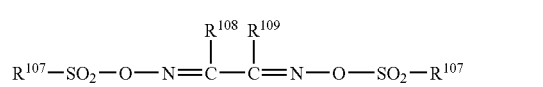

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

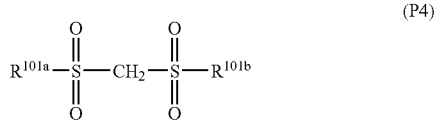

Herein $R^{101a}$ and $R^{101b}$ are as defined above.

(v) Sulfonic Acid Esters of N-hydroxyimide Compounds of Formula (P5)

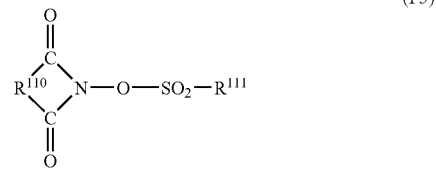

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; and the alkoxy groups of 1 to 4 carbon atoms include methoxy, ethoxy, propoxy, isopropoxy, n-butoxy, isobutoxy, and tert-butoxy. The phenyl groups which may have substituted thereon an alkyl or alkoxy of 1 to 4 carbon atoms, nitro, or acetyl include phenyl, tolyl, p-tert-butoxyphenyl, p-acetylphenyl and p-nitrophenyl. The hetero-aromatic groups of 3 to 5 carbon atoms include pyridyl and furyl.

Illustrative examples of the photoacid generator include: onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethane-sulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethane-sulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethane-sulfonate, (2-norbornyl)methyl(2-oxocyclohexyl)sulfonium trifluoro-methanesulfonate, ethylenebis[methyl(2-oxocyclopentyl)sulfonium trifluoro-methanesulfonate], and 1,2'-naphthylcarbonylmethyltetrahydrothiophenium triflate;

diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethylglyoxime, bis-O-(trifluoromethanesulfonyl)-α-dimethylglyoxime, bis-O-(1,1,1-trifluoroethanesulfonyl)-α-dimethylglyoxime, bis-O-(tert-butanesulfonyl)-α-dimethylglyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexylcarbonyl-2-(p-toluenesulfonyl)propane and 2-isoptopylcarbonyl-2-(p-toluenesulfonyl)propane;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethane-sulfonate, (2-norbornyl)methyl(2-oxocylohexyl)sulfonium trifluoro-methanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-O-(p-toluenesulfonyl)-α-dimethylglyoxime and bis-O-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

Also included are the oxime sulfonates described in U.S. Pat. No. 6,004,724, for example, (5-(4-toluenesulfonyl)oxyimino-5H-thiophen-2-ylidene)phenyl-acetonitrile, (5-(10-camphorsulfonyl)oxyimino-5H-thiophen-2-ylidene)phenyl-acetonitrile, (5-n-octanesulfonyloxyimino-5H-thiophen-2-ylidene)phenyl-acetonitrile, (5-(4-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, etc.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphoryl-sulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethylphenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethylphenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4- methoxyphenyl)-ethanone oxime-O-(4-methoxyphenyl)sulfonate; 2,2,2-trifluoro-1-(4-methoxyphenyl)-ethanone oxime-O-(4-dodecylphenyl)-sulfonate; 2,2,2-trifluoro-1-(4-methoxyphenyl)-ethanone oxime-O-octylsulfonate; 2,2,2-trifluoro-1-(4-thiomethyl-phenyl)-ethanone oxime-O-(4-methoxyphenyl)sulfonate; 2,2,2-trifluoro-1-(4-thiomethylphenyl)-ethanone oxime-O-(4-dodecylphenyl)sulfonate; 2,2,2-trifluoro-1-(4-thiomethyl-phenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl)-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propyl-sulfonate; 2,2,2-trifluoro-1-[4-methylsulfonylphenyl]-ethanone oxime-O-propylsulfonate; 1,3-bis[1-(4-phenoxyphenyl)-2,2,2-trifluoroethanone oxime-O-sulfonyl]phenyl; 2,2,2-trifluoro-1-[4-methylsulfonyl-oxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; and 2,2,2-trifluoro-1-[1-dioxathiophen-2-yl)]-ethanone oxime-O-propylsulfonate.

Also included are the oxime sulfonates described in JP-A 9-95479 and JP-A 9-230588 and the references cited therein, for example, α-(p-toluenesulfonyloxyimino)-phenylacetonitrile, α-(p-chlorobenzenesulfonyloxyimino)-phenylacetonitrile, α-(4-nitrobenzenesulfonyloxyimino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylacetonitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl]-acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Suitable bisoxime sulfonates include those described in JP-A 9-208554, for example, bis(α-(4-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(4-toluenesulfonyloxy)imino)-p-phenylenediacetonitrile, bis(α-(trifluoromethanesulfonyloxy)imino)-p-phenylene-diacetonitrile, bis(α-(4-methoxybenzenesulfonyloxy)imino)-p-phenylene-diacetonitrile, bis(α-(4-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(4-toluenesulfonyloxy)imino)-m-phenylenediacetonitrile, bis(α-(trifluoromethanesulfonyloxy)imino)-m-phenylene-diacetonitrile, bis(α-(4-methoxybenzenesulfonyloxy)imino)-m-phenylene-diacetonitrile, etc.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 50 parts, and especially 0.5 to 40 parts by weight, per 100 parts by weight of the base resin (all parts are by weight, hereinafter). Less than 0.1 part of the photoacid generator may generate a less amount of acid upon exposure, sometimes leading to a poor sensitivity and resolution whereas more than 50 parts of the photoacid generator may adversely affect the transmittance and resolution of resist.

Component C

The organic solvent (C) used herein may be any organic solvent in which the base resin, photoacid generator, and other components are soluble. Illustrative, non-limiting, examples of the organic solvent include ketones such as cyclohexanone and methyl isopentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, cyclohexanone, or a mixture thereof because the photoacid generator is most soluble therein.

An appropriate amount of the organic solvent used is about 200 to 1,000 parts, especially about 400 to 800 parts by weight per 100 parts by weight of the base resin.

Component D

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

The basic compound is preferably formulated in an amount of 0.001 to 2 parts, and especially 0.01 to 1 part by weight, per 100 parts by weight of the base resin. Less than 0.001 part of the basic compound achieves no or little addition effect whereas more than 2 parts would result in too low a sensitivity.

While the resist composition of the invention is basically composed of the inventive polymer, the photoacid generator, the organic solvent and optionally the basic compound as described above, it may further include any well-known components such as dissolution inhibitors, acidic compounds, stabilizers, dyes, and surfactants, if necessary.

Pattern formation using the resist composition of the -invention may be carried out by a known lithographic technique. For example, the resist composition is applied onto a substrate such as a silicon wafer by spin coating or the like to form a resist film having a thickness of 0.3 to 2.0 µm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm$^2$, and preferably about 10 to 100 mJ/cm$^2$, then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5 wt % (preferably 2 to 3 wt %) aqueous solution of tetramethylammonium hydroxide (TMAH), this being done by a conventional technique such as dip, puddle, or spray technique for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV or excimer laser radiation having a wavelength of 248 to 157 nm, x-rays, or an electron beam. The desired pattern may not be obtainable outside the upper and lower limits of the above range.

EXAMPLE

Examples of the invention are given below by way of illustration and not by way of limitation.

Example 1

Synthesis of 2-methyl-3,3,5,5,5-pentafluoro-2,4,4-trihydroxypentyl methacrylate

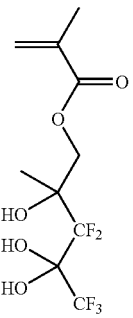

Under nitrogen atmosphere and at 5° C., 129 ml of 1.6M n-butyllithium in hexane was added to a mixture of 16.8 g of 1,1,1,3,3,3-hexafluoro-2-propanol and 120 g of tetrahydrofuran, which was stirred for one hour at 5° C. Next, 14.2 g of 2-oxopropyl methacrylate was added at 5° C. The mixture was stirred for 10 hours, after which dilute hydrochloric acid was added to stop the reaction and neutralize the reaction mixture. Through conventional aqueous work-up and purification by silica gel column chromatography, 25.3 g of the target compound was obtained (yield 82%).

2-methyl-3,3,5,5,5-pentafluoro-2,4,4-trihydroxypentyl methacrylate

Colorless Solid

IR (KBr): ν=3380, 3006, 2970, 1697, 1639, 1471, 1457, 1394, 1382, 1363, 1330, 1307, 1274, 1209, 1172, 1116, 1089, 1020, 993, 973, 950, 904, 819, 744, 698 cm$^{-1}$
$^1$H-NMR (600 MHz in DMSO-d6): δ=1.37 (3H, s), 1.89 (3H, m), 4.27 (1H, d, J=11.3 Hz), 4.34 (1H, d, J=11.3 Hz), 5.70 (1H, m), 6.09 (1H, m), 6.34 (1H, s), 7.85 (1H, s), 7.99 (1H, s) $^{19}$F-NMR (565 MHz in DMSO-d6): δ=−121.7 (1F, dq, J=264.5, 13.4 Hz), −120.6 (1F, dq, J=264.5, 11.9 Hz), −80.6 (3F, dd, J=13.4, 11.9 Hz)

Example 2

Synthesis of 2,4-dihydroxy-2-methyl-3,3,5,5,5-pentafluoro-pentyl methacrylate

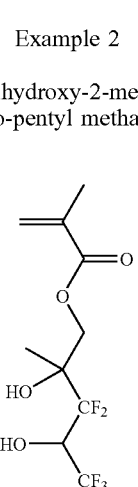

To a mixture of 30.8 g of 2-methyl-3,3,5,5,5-pentafluoro-2,4,4-trihydroxypentyl methacrylate obtained in Example 1 and 300 g of methylene chloride was added 8.7 g of borane-t-butylamine complex, followed by 24 hours of stirring. Dilute hydrochloric acid was added to stop the reaction. Through conventional aqueous work-up and purification by silica gel column chromatography, 26.6 g of the target compound was obtained (yield 91%).

2,4-dihydroxy-2-methyl-3,3,5,5,5-pentafluoropentyl methacrylate

IR (thin film): ν=3432, 2996, 2964, 2935, 1706, 1637, 1456, 1407, 1380, 1328, 1301, 1276, 1174, 1112, 1037, 1020, 950, 885, 813, 673 cm$^{-1}$ $^1$H-NMR (600 MHz in DMSO-d6) main isomer's spectrum: δ=1.30 (3H, s), 1.89 (3H, m), 4.11 (1H, d, J=11.3 Hz), 4.26 (1H, d, J=11.3 Hz), 4.66 (1H, m), 5.70 (1H, m), 6.04 (1H, s), 6.09 (1H, s), 7.30 (1H, d, J=7.9 Hz) $^{19}$F-NMR (565 MHz in DMSO-d6) main isomer's spectrum: δ=−126.1 (1F, m), −120.3 (1F, dq, J=262.4, 17.3 Hz), −73.5 (3F, m)

Example 3

Synthesis of 4-methyl-5,5,7,7,7-pentafluoro-4,6,6-trihydroxyheptyl methacrylate

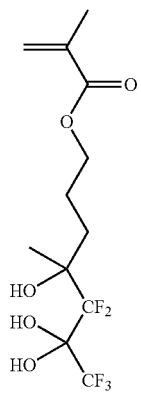

By repeating the procedure of Example 1 except that 4-oxopentyl methacrylate was used instead of the 2-oxopropyl methacrylate, the target compound was obtained (yield 70%).

4-methyl-5,5,7,7,7-pentafluoro-4,6,6-trihydroxyheptyl methacrylate

EI-MS: m/z=43, 69, 87, 117, 231 CI-MS (isobutane): m/z=87, 233, 319

Example 4

Synthesis of 4,6-dihydroxy-4-methyl-5,5,7,7,7-pentafluoro-heptyl methacrylate

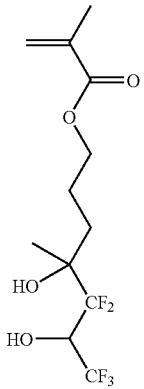

By repeating the procedure of Example 1 except that an equimolar amount of 4-oxopentyl methacrylate was used instead of 2-methyl-3,3,5,5,5-pentafluoro-2,4,4-trihydroxypentyl methacrylate, the target compound was obtained (yield 70%).

4,6-dihydroxy-4-methyl-5,5,7,7,7-pentafluoroheptyl methacrylate

IR (KBr): ν=3426, 2967, 2935, 2900, 1700, 1635, 1454, 1405, 1378, 1328, 1303, 1280, 1178, 1095, 1014, 948, 871, 838, 817, 759, 659 cm$^{-1}$ $^1$H-NMR (600 MHz in DMSO-d6) main isomer's spectrum: δ=1.20 (3H, s), 1.50–1.80 (4H, m), 1.87 (3H, m), 4.00–4.15 (2H, m), 4.63 (1H, m), 5.41 (1H, s), 5.66 (1H, m), 6.01 (1H, m), 7.07 (1H, m) $^{19}$F-NMR (565 MHz in DMSO-d6) main isomer's spectrum: δ=−125.9 (1F, m), −121.1 (1F, dq, J=258.0, 18.1 Hz), −73.5 (3F, m)

Example 5

Synthesis of 4-(2,2-dihydroxy-1,1,3,3,3-pentafluoropropyl)-4-hydroxycyclohexyl methacrylate

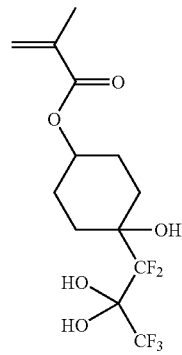

By repeating the procedure of Example 1 except that an equimolar amount of 4-oxocyclohexyl methacrylate was used instead of the 2-oxopropyl methacrylate in Example 1, the target compound was obtained (yield 64%).

4-(2,2-dihydroxy-1,1,3,3,3-pentafluoropropyl)-4-hydroxycyclohexyl methacrylate

EI-MS: m/z=41, 69, 87, 97, 129, 207, 243 CI-MS (isobutane): m/z=87, 129, 183, 205, 227, 245, 331

Example 6

Synthesis of [4-hydroxy-4-(2-hydroxy-1,1,3,3,3-pentafluoro-propyl)cyclohexyl]methyl methacrylate

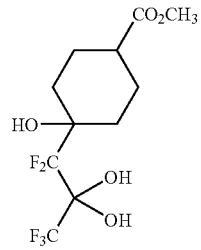

Colorless Solid

IR (KBr): ν=3376, 3328, 3102, 2964, 1698, 1444, 1207, 1164, 1064, 815, 736 cm$^{-1}$ $^1$H-NMR (600 MHz in DMSO-d6) main isomer's spectrum: δ=1.60–1.94 (6H, m), 2.29–2.37 (1H, m), 3.62 (3H, s), 6.35 (1H, br.s, OH), 7.92 (2H, br.s, hydrate-2OH) ppm $^{19}$F-NMR (565 MHz in DMSO-d6, trifluoroacetic acid standard): δ=−135.6 (2×0.1F, dq-like, J=54, 8 Hz), −123.5 (2×0.9F, q, J=13 Hz), −82.1 (3×0.1F, t, J=8 Hz), −81.0 (3×0.89F, t, J=13 Hz) ppm <6-2> Synthesis of 4-hydroxy-4-(2-hydroxy-1,1,3,3,3-pentafluoropropyl)cyclohexanemethanol

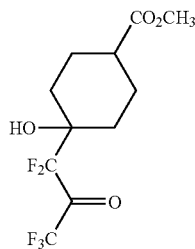

In 300 ml of toluene was dissolved 30.0 g of methyl 4-hydroxy-4-(2,2-dihydroxy-1,1,3,3,3-pentafluoropropyl)-cyclohexanecarboxylate obtained in <6-1>. The solution was stirred and heated under reflux while the water formed was continuously removed. Under nitrogen atmosphere and with stirring, this solution was added dropwise to a solution of 5.0 g lithium aluminum hydride in 100 ml tetrahydrofuran. The mixture was stirred at 5° C. for one hour and then at room temperature for 18 hours. The reaction mixture was combined with 500 ml of 10% hydrochloric acid and extracted with ethyl acetate. Through conventional work-up including washing, drying and concentration, a crude product was obtained. Recrystallization from n-hexane gave 20.8 g (yield 80%) of the target compound.

4-hydroxy-4-(2-hydroxy-1,1,3,3,3-pentafluoropropyl)-cyclohexane methanol (92:8 diastereomer mixture) colorless solid IR (KBr): ν=3444, 3363, 3009, 2944, 2875, 1384, 1292, 1216, 1180, 1157, 1126, 1108, 1074, 929, 840 cm$^{-1}$ $^1$H-NMR (600 MHz in DMSO-d6) main isomer's spectrum: δ=1.18–1.90 (9H, m), 3.24 (2H, d, J=6.2 Hz), 4.43 (1H, br.s), 4.63–4.73 (1H, m), 5.30 (1H, s, OH), 7.03 (1H, d, J=8.2 Hz, OH) ppm $^{19}$F-NMR (565 MHz in DMSO-d6, trifluoroacetic acid standard) main isomer's spectrum: δ=−127.4 (1F, dd, J=16, 257 Hz), −122.7 (1F, dq, J=257, 18 Hz), −73.0 (3F, dt-like, J=7, 18 Hz) ppm- <6-1> Synthesis of methyl 4-hydroxy-4-(2-oxo-1,1,3,3,3-pentafluoropropyl)cyclohexanecarboxylate equivalent

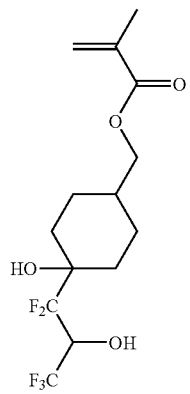

With stirring under nitrogen atmosphere, a mixture of 102.5 g of 1,1,1,3,3,3-hexafluoro-2-propanol and 800 ml of tetrahydrofuran was cooled to 5° C. To the mixture, 500 ml of 2.44M n-butyllithium in n-hexane was added dropwise. The mixture was stirred at 5° C. for 90 minutes. To the reaction mixture, 78.1 g of methyl cyclohexanone-4-carboxylate in 100 ml of tetrahydrofuran was added. The mixture was stirred at 5° C. for 1 hour and then at room temperature for 18 hours. The reaction mixture was combined with 500 ml of 10% hydrochloric acid and extracted with ether. Crude crystals were obtained through conventional work-up including washing, drying and concentration. Recrystallization from n-hexane gave 150.8 g (yield 94%) of a hydrate which was an equivalent of the target compound.

methyl 4-hydroxy-4-(2,2-dihydroxy-1,1,3,3,3-pentafluoropropyl)cyclohexanecarboxylate (9:1 diastereomer mixture)

<6-3> Synthesis of [4-hydroxy-4-(2-hydroxy-1,1,3,3,3-pentafluoropropyl)cyclohexyl]methyl methacrylate

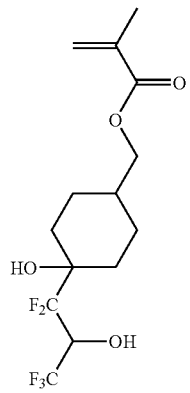

A mixture of 2.0 g of 4-hydroxy-4-(2-hydroxy-1,1,3,3,3-pentafluoropropyl)cyclohexanemethanol obtained in <6-2>, 1.0 g of methacrylic acid, 30 mg of p-toluenesulfonyl chloride, and 50 ml of toluene was stirred and heated under reflux while the water formed was continuously removed. After water ceased to distill out, heating under reflux was continued for a further 2 hours. The reaction mixture was cooled, poured into 100 ml of saturated sodium chloride water, and extracted with diethyl ether. Through conventional work-up including washing, drying and concentration, a crude product was obtained. Recrystallization from n-hexane gave 1.67 g (yield 67%) of the target fluorinated ester compound.

[4-hydroxy-4-(2-hydroxy-1,1,3,3,3-pentafluoropropyl)-cyclohexyl]methyl methacrylate (95:5 diastereomer mixture) colorless solid EI-MS: (m/z)$^+$=41, 69, 93, 111, 143, 197, 242, 260, 346 (M$^+$) IR (KBr): ν=3610, 3484, 3421, 2940, 1700, 1635, 1454, 1336, 1274, 1216, 1176, 1155, 1132, 1112, 1066, 1004 cm$^{-1}$ $^1$H-NMR (600 MHz in DMSO-d6) main isomer's spectrum: δ=1.32–1.47 (3H, m), 1.52–1.69 (4H, m), 1.77–1.83 (1H, m), 1.88–1.92 (1H, m), 1.92 (3H, s), 3.96 (1H, d, J=6.5 Hz), 4.64–4.74 (1H, m), 5.39 (1H, s-like, OH), 5.71 (1H, t, J=1 Hz), 6.07 (1H, s-like), 7.07 (1H, br.d, OH) ppm $^{13}$C-NMR (150 MHz in DMSO-d6) main isomer's spectrum: δ=19.51, 24.79 (d, J=19 Hz), 29.24 (d, J=6 Hz), 31.01 (d, J=4 Hz), 37.29, 67.23–68.15 (m), 70.27, 74.01 (t, J=25 Hz), 122.00 (dd, J=251, 262 Hz), 125.68 (q, J=285 Hz), 127.09, 168.04 ppm $^{19}$F-NMR (565 MHz in DMSO-d6, trifluoroacetic acid standard) main isomer's spectrum: δ=−127.9 (1F, dd, J=18, 257 Hz), −123.2 (1F, dq, J=258, 18 Hz), −73.5 (3F, dt-like, J=7, 18 Hz) ppm Example 7

Synthesis of 4-hydroxy-4-(2-hydroxy-1,1,3,3,3-pentafluoro-propyl)cyclohexyl methacrylate <7-1> Synthesis of 4-hydroxy-4-(2-oxo-1,1,3,3,3-pentafluoro-propyl)cyclohexanone equivalent

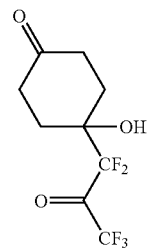

Reaction was performed as in <6-1> aside from using 48.0 g of cyclohexane-1,4-dione monoethylene acetal instead of the methyl cyclohexanone-4-carboxylate in <6-1>. To the reaction mixture where 4-ethylenedioxy-1-(2-oxo-1,1,3,3,3-pentafluoropropyl)cyclohexanol formed, 15 ml of acetone and 500 ml of 10% hydrochloric acid were added. The mixture was stirred at 40° C. for 24 hours. After cooling, the organic layer was separated, from which a crude product was obtained through conventional work-up including washing, drying and concentration. Recrystallization from n-hexane gave 77.5 g (yield 91%) of a hydrate which was an equivalent of the target compound.

4-hydroxy-4-(2,2-dihydroxy-1,1,3,3,3-pentafluoropropyl)-cyclohexanone

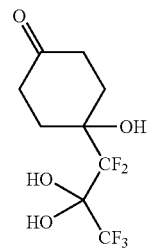

Colorless Solid

IR (KBr): ν=3459, 3276, 2996, 1698, 1450, 1240, 1203, 1153, 1081, 958 cm$^{-1}$ $^1$H-NMR (600 MHz in DMSO-d6): δ=2.09–2.20 (4H, m), 2.22–2.28 (2H, m), 2.56–2.66 (2H, m), 6.37 (1H, br.s, OH), 7.96 (2H, br.s, 2OH) ppm $^{19}$F-NMR (565 MHz in DMSO-d6, trifluoroacetic acid standard): δ=−122.0 (2F, q, J=13 Hz), −80.6 (3F, t, J=13 Hz) ppm <7-2> Synthesis of 1-(2-hydroxy-1,1,3,3,3-pentafluoropropyl)-cyclohexane-1,4-diol

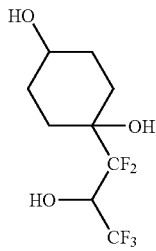

In 80 ml of toluene was dissolved 10.0 g of 4-hydroxy-4-(2,2-dihydroxy-1,1,3,3,3-pentafluoropropyl)cyclohexanone obtained in <7-1>. The solution was heated under reflux. The water formed was removed, leaving a toluene solution of 4-hydroxy-4-(2-oxo-1,1,3,3,3-pentafluoropropyl)cyclohexanone. Under nitrogen and with stirring at room temperature, this solution was added dropwise to a solution of 3.3 g lithium aluminum hydride in 100 ml tetrahydrofuran. The reaction mixture was stirred at room temperature for 24 hours and then cooled to 5° C. The reaction mixture was combined with 100 ml of ethyl acetate and then with 100 ml of 20% hydrochloric acid. The mixture was stirred at room temperature for 3 hours and then extracted with toluene. Through conventional work-up including washing, drying and concentration, 8.0 g (yield 84%) of the target compound was obtained.

1-(2-hydroxy-1,1,3,3,3-pentafluoropropyl)cyclohexane-1,4-diol

EI-MS: $(m/z)^+$=41, 55, 69, 97, 115, 246 $[(M-H_2O)^+]$

<7-3> Synthesis of 4-hydroxyl-4-(2-hydroxy-1,1,3,3,3-pentafluoropropyl)cyclohexyl methacrylate By repeating the procedure of <6-3> aside from using 1-(2-hydroxy-1,1,3,3,3-pentafluoropropyl)cyclohexane-1,4-diol obtained in <7-2> instead of the 4-hydroxy-4-(2-hydroxy-1,1,3,3,3-pentafluoropropyl)cyclohexane methanol used in <6-3>, the target compound was obtained (yield 64%).

4-hydroxyl-4-(2-hydroxy-1,1,3,3,3-pentafluoropropyl)-cyclohexyl methacrylate

EI-MS: (m/z)+=41, 69, 79, 87, 97, 129, 183, 228, 314 $[(M-H_2O)^+]$CI-MS (isobutane): $(m/z)^+$=87, 229, 247, 333

Example 8

Synthesis of poly([4-hydroxy-4-(2-hydroxy-1,1,3,3,3-pentafluoropropyl)cyclohexyl]methyl methacrylate) homopolymer Under nitrogen atmosphere, a mixture of 5.00 g of [4-hydroxyl-4-(2-hydroxy-1,1,3,3,3-pentafluoropropyl)-cyclohexyl]methyl methacrylate, 23 mg of 2-mercaptoethanol and 20.00 g of tetrahydrofuran was stirred at 60° C., to which 47 mg of 2,2'-azobisisobutyronitrile was added. While keeping at 60° C., the mixture was stirred for a further 20 hours. The polymerization solution was cooled to room temperature and with vigorous stirring, added dropwise to 500 ml of n-hexane. The resulting solids were collected by filtration and dried in vacuo at 50° C. for 15 hours, leaving 4.55 g (yield 91%) of a polymer in white solid powder form. The polymer had a weight average molecular weight (Mw) of 18,600 as measured by GPC versus polystyrene standards.

A polymer solution was prepared by dissolving 1 g of the homopolymer in 10 g of propylene glycol monomethyl ether acetate (PGMEA) and passing through a filter with a pore size of 0.2 μm. It was spin coated onto a 8-inch diameter silicon wafer and baked on a hot plate at 110° C. for 60 seconds, forming a polymer film of 300 nm thick. Using a dissolution rate-measuring device Model RDA-790 (by Lithotec Japan Co., Ltd.), the dissolution rate of the polymer film in a 2.38 wt % tetramethylammonium hydroxide aqueous solution was measured. The dissolution rate was 72.5 angstrom/sec, indicating that the polymer performs well as an alkali-soluble resin.

Example 9

Synthesis of poly(3-ethyl-3-exo-tetracyclo[4.4.0.1²,⁵.1⁷,¹⁰]-dodecyl methacrylate-co-3-hydroxyl-1-adamantyl methacrylate-co-4,8-dioxatricyclo[4.2.1.0³,⁷]nonan-5-on-2-yl methacrylate-co-[4-hydroxy-4-(2-hydroxy-1,1,3,3,3-pentafluoropropyl)-cyclohexyl]methyl methacrylate)

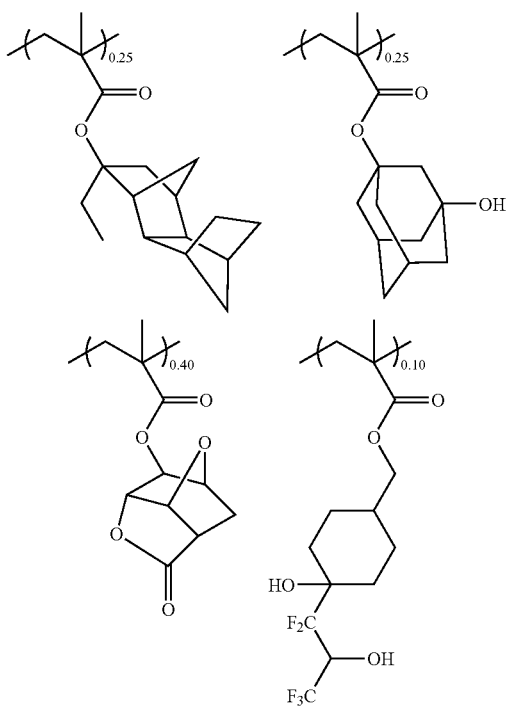

With stirring at 80° C., a solution was added dropwise over 4 hours to 11.67 g of propylene glycol monomethyl ether acetate (PGMEA) under nitrogen atmosphere. The solution added contained 5.50 g of 3-ethyl-3-exo-tetracyclo[4.4.0.1²,⁵.1⁷,¹⁰]dodecyl methacrylate, 4.69 g of 3-hydroxyl-1-adamantyl methacrylate, 7.12 g of 4,8-dioxatricyclo[4.2.1.0³,⁷]nonan-5-on-2-yl methacrylate, 2.75 g of [4-hydroxy-4-(2-hydroxy-1,1,3,3,3-pentafluoro-propyl)cyclohexyl]methyl methacrylate, 521 mg of 2,2'-azobisisobutyronitrile, and 93.0 mg of 2-mercaptoethanol in 35.0 g of PGMEA. The mixture was stirred at 80° C. for a further 2 hours. The reaction mixture was cooled to room temperature and with vigorous stirring, added dropwise to 1,000 ml of n-hexane. The resulting solids were collected by filtration and dried in vacuo at 50° C. for 15 hours, leaving 18.39 g (yield 92%) of a polymer in white solid powder form.

The polymer had a copolymerization ratio of approximately 25.3/9.3/23.2/42.2 as computed from an integration ratio of ¹H-NMR spectrum and a weight average molecular weight (Mw) of 7,000 as measured by GPC versus polystyrene standards.

Resolution as Resist Material

A resist solution was prepared by mixing 80 parts by weight of the polymer of Example 9, 2.18 parts by weight of triphenylsulfonium nonafluorobutanesulfonate as a photoacid generator, 0.472 part by weight of tris-methoxymethoxy-ethylamine as a basic compound, and 640 parts by weight of PGMEA (containing 0.01 wt % of surfactant KH-20 by Asahi Glass Co., Ltd.) as a solvent and passing through a Teflon® filter with a pore diameter of 0.2 μm.

The resist solution was spin-coated on a silicon wafer having an antireflective coating (ARC29A by Nissan Chemical Industries Ltd., 78 nm) coated thereon, and heat treated at 130° C. for 60 seconds to form a resist film of 300 nm thick. The resist film was exposed on an ArF excimer laser stepper (Nikon Corp., NA=0.68), heat treated at 105° C. for 60 seconds, and puddle-developed in a 2.38 wt % tetramethylammonium hydroxide aqueous solution for 60 seconds, forming a 1:1 line-and-space pattern. The developed wafer was cut, and the cross section was observed under a scanning electron microscope (SEM). Provided that the optimum dose (Eop, mJ/cm²) is defined as the dose which provides a 1:1 resolution at the top and bottom of a 0.13 μm line-and-space pattern and the resolution is defined as the minimum line width (μm) of the lines and spaces that separate at this dose, the resist showed an optimum dose of 25 mJ/cm², a minimum line width of 0.11 μm, and good pattern rectangularity. It is demonstrated that the resist material within the scope of the invention has a high resolution upon ArF excimer laser exposure.

Japanese Patent Application No. 2004-203195 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A polymerizable fluorinated ester compound having the general formula (1) or (2):

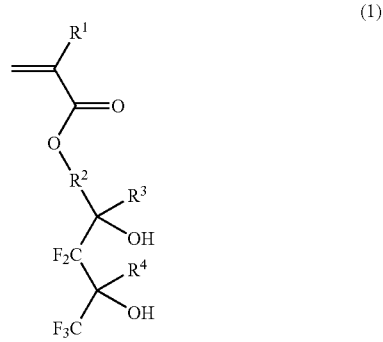

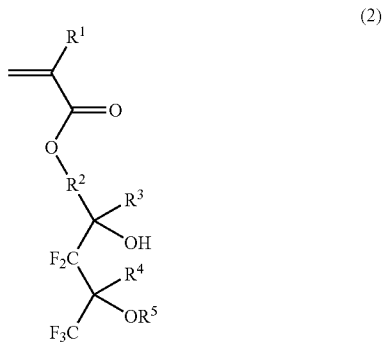

wherein $R^1$ is hydrogen, methyl or trifluoromethyl, $R^2$ is a straight, branched or cyclic, divalent hydrocarbon group of 1 to 15 carbon atoms, $R^3$ is hydrogen or a straight, branched or cyclic, monovalent hydrocarbon group of 1 to 15 carbon atoms, or $R^2$ and $R^3$, taken together, may form a ring with the carbon atom to which they are attached, $R^4$ is hydrogen, hydroxyl or a straight, branched or cyclic, monovalent hydrocarbon group of 1 to 15 carbon atoms, and $R^5$ is an acid labile group.

2. The polymerizable fluorinated ester compound of claim 1 wherein $R^2$ is a divalent hydrocarbon group containing a cycloaliphatic hydrocarbon of 5 to 12 carbon atoms.

3. The polymerizable fluorinated ester compound of claim 1 wherein $R^2$ is —$(CH_2)_n$— wherein n is an integer of 1 to 8.

4. The polymerizable fluorinated ester compound of claim 1 wherein $R^2$ and $R^3$, taken together, form a trivalent cycloaliphatic hydrocarbon group of 5 to 12 carbon atoms with the carbon atom to which they are attached.

5. The polymerizable fluorinated ester compound of claim 1, wherein $R^2$ is hydrogen or a straight, branched, or cyclic monovalent hydrocarbon group of 1 to 15 carbon atoms.

* * * * *